US005998398A

United States Patent [19]
Daluge et al.

[11] Patent Number: 5,998,398
[45] Date of Patent: Dec. 7, 1999

[54] 2-AMINO-5,6-DICHLOROBENZIMIDAZOLE DERIVATIVES HAVING ANTIVIRAL ACTIVITY

[75] Inventors: Susan Mary Daluge, Chapel Hill; Marc Werner Andersen, Raleigh, both of N.C.

[73] Assignee: Glaxo Wellcome Inc., Research Triangle Park, N.C.

[21] Appl. No.: 09/101,101

[22] PCT Filed: Jan. 3, 1997

[86] PCT No.: PCT/EP97/00018

§ 371 Date: Jul. 1, 1998

§ 102(e) Date: Jul. 1, 1998

[87] PCT Pub. No.: WO97/25316

PCT Pub. Date: Jul. 17, 1997

[30] Foreign Application Priority Data

Jan. 5, 1996 [GB] United Kingdom .................... 9600142

[51] Int. Cl.[6] ..................................................... A01N 43/00
[52] U.S. Cl. .......................... 514/210; 514/394; 514/395; 548/306.1; 548/307.4; 548/310.4
[58] Field of Search .............. 548/306.1, 307.4, 548/310.4; 514/210, 394, 395

[56] References Cited

U.S. PATENT DOCUMENTS

| | | | |
|---|---|---|---|
| 4,492,708 | 1/1985 | Spitzer . | |
| 5,039,689 | 8/1991 | Daluge | 514/359 |
| 5,248,672 | 9/1993 | Townsend et al. | 514/43 |
| 5,339,580 | 8/1994 | Daluge | 514/394 |
| 5,399,580 | 3/1995 | Daluge | 514/394 |
| 5,534,535 | 7/1996 | Townsend et al. | 514/394 |

FOREIGN PATENT DOCUMENTS

| | | |
|---|---|---|
| 0334361 A3 | 9/1989 | European Pat. Off. . |
| 0347852 A2 | 12/1989 | European Pat. Off. . |
| 0368640 A3 | 5/1990 | European Pat. Off. . |
| 0431799 A2 | 6/1991 | European Pat. Off. . |
| 0434450 A2 | 6/1991 | European Pat. Off. . |
| 0521463A | 1/1993 | European Pat. Off. . |
| 3-223 264A | 10/1991 | Japan . |
| 92/07867 | 5/1992 | WIPO . |
| 93/18009 | 9/1993 | WIPO . |
| 94/08456 | 4/1994 | WIPO . |
| 96/01833 | 1/1996 | WIPO . |
| 96/07646 | 3/1996 | WIPO . |

OTHER PUBLICATIONS

Database WPI, Section Ch. Week 9146, Derwent Publications Ltd., London, GB; AN 91–335122, XP002029298.
Marx, Jean, "CMV–p53 Interaction May Help Explain Clogged Arteries," Science, vol. 265, p. 320 (Jul. 15, 1994).
Speir, et al., "Potential Role of Human Cytomegalovirus and p53 Interaction in Coronary Restenosis," Science, vol. 265, pp. 391–394 (Jul. 15, 1994).
Steyn et al., "Studies on Cyclitols—Synthesis and Stereochemistry of Cyclopentanetriols and Related Epoxycyclanols", Tetrahedron, vol. 25, pp. 3579 to 3597 (Mar. 6, 1969).
McCollum, "Viral Infections of Humans", Ch. 12 (second edition, Ed.Evans,A.S.), pp. 327–350 (1982).
Townsend et al., "Benzimidazole Nuclesides, Nucleotides, and related Derivatives", Chemical Reviews, vol. 70, No. 3, pp. 389–438 no month available(1970).
Bruckner et al., "Automated Enantioseparation of Amino Acids by Derivatization with o–Phthaldialdehyde and N–Acylated Cysteines", Journal of Chromatography, 476, pp. 73–82 no month available(1989).
Averett, "Anti–HIV compound assessment by two novel high capacity assays", Journal of Virological Methods, 23, pp. 263–276, no month available(1989).
Saiki, et al., "Primer–Directed Enzymatic Amplification of DNA with a Thermostable DNA Polymerase", Science, vol. 239, pp. 487–491, (Jan. 29, 1988).
Tyle, "Iontophoretic Devices for Drug Delivery", Pharmaceutical Research, 3(6), pp. 318–326, no month available, 1986.
Vince, et al., "Puromycin Analogs.[1] Studies on Ribosomal Binding with Diastereomeric Carbocyclic Puromycin Analogs", Journal of Medicinal Chemistry, vol. 17, No. 6, pp. 578–583, no month available, 1974.
Jagt, et al., "Diels–alder Cycloadditions of Sulfonyl Cyanides with Cyclopentadiene,Synthesis of 2–Azabicyclo [2.2.1]hepta–2,5–dienes", J. Org. Chem., vol. 39, No. 4, 564–566, no month, 1974.
Holodinity et al., "Detection and Quantification of Gene Amplification Products by a Nonisotopic Automated system", Bio Techniques, 12(1) pp. 37–39 no month available (1992).
Depres et al., "Improved Selectivity in the Preparation of Some 1,1–Difunctionalized 3–Cyclopentenes. High–Yield Synthesis of 3–Cyclopentenecarboxylic Acid", J. Org. Chem., 49, 928–931, no month available (1984).

Primary Examiner—Fiona T. Powers
Attorney, Agent, or Firm—Lorie Ann Morgan

[57] ABSTRACT

The present invention relates to benzimidazole derivatives of formula (I) wherein: $R^1$ represents H, $C_{1-4}$alkyl, $C_{3-5}$cycloalkyl; $R^2$ represents H, $C_{1-4}$ alkyl; or $R^1$ and $R^2$ together form with the nitrogen a 4 or 5 membered heterocyclic ring; $R^3$ represents $BR^4$ or $R^4$ wherein B represents a bridging group —C(O)NH—, —C(O)N$C_{1-4}$ alkyl-, or C(O)O— and $R^4$ represents H, $C_{1-4}$alkyl, $C_{2-6}$alkenyl or halo (preferably fluoro); and each n is an integer independently selected from 0, 1, or 2 (preferably 0 or 1); and geometric isomers or mixtures thereof; and physiologically functional derivatives thereof, and their use in medical therapy particularly for the treatment or prophylaxis of virus infections such as those caused by herpes viruses. The invention also relates to their preparation and pharmaceutical formulations containing them.

13 Claims, No Drawings

2-AMINO-5,6-DICHLOROBENZIMIDAZOLE DERIVATIVES HAVING ANTIVIRAL ACTIVITY

This application is filed pursuant to 35 U.S.C. § 371 as a United States National Phase Application of International Application No. PCT/EP97/00018 filed Jan. 3, 1997, which claims priority from 9600142.5 GB filed Jan. 5, 1996.

The present invention relates to benzimidazole derivatives and their use in medical therapy particularly for the treatment or prophylaxis of virus infections such as those caused by herpes viruses. The invention also relates to their preparation and pharmaceutical formulations containing them.

Of the DNA viruses, those of the herpes group are the sources of the most common viral illnesses in man. The group includes herpes simplex virus types 1 and 2 (HSV), varicella zoster virus (VZV), cytomegalovirus (CMV), Epstein-Barr virus (EBV), human herpes virus type 6 (HHV-6) and human herpes virus type 7 (HHV-7). HSV-1 and HSV-2 are some of the most common infectious agents of man. Most of these viruses are able to persist in the host's neural cells; once infected, individuals are at risk of recurrent clinical manifestations of infection which can be both physically and psychologically distressing.

In common with other herpes viruses, infection with CMV leads to a lifelong association of virus and host Congenital infection following infection of the mother during pregnancy may give rise to clinical effects such as death or gross disease (microcephaly, hepatosplenomegaly, jaundice, mental retardation), retinitis leading to blindness or, in less severe forms, failure to thrive, and susceptibility to chest and ear infections. CMV infection in patients who are immunocompromised for example as a result of malignancy, treatment with immunosuppressive drugs following transplantation or infection with Human Immunodeficiency Virus may give rise to refinitis, pneumonifts, gastrointestinal disorders and neurological diseases.

It has now been found that certain substituted benzimidazole compounds referred to below have activity against viruses particularly CMV. According to one aspect the present invention provides compounds of formula (I)

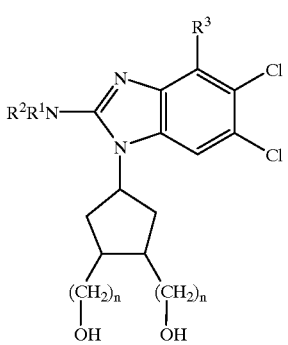

(I)

wherein:
$R^1$ represents;
H, $C_{1-4}$alkyl, $C_{3-5}$cycloalkyl;
$R^2$ represents;
H, $C_{1-4}$alkyl; or
$R^1$ and $R^2$ together form with the nitrogen a 4 or 5 membered heterocyclic ring;
$R^3$ represents $BR^4$ or $R^4$, wherein B represents a bridging group —C(O)NH—, —C(O)N$C_{1-4}$alkyl-, or —C(O)O— and $R^4$ represents H, $C_{1-4}$alkyl, $C_{2-6}$alkenyl or halo (preferably fluoro); and each n is independently selected from an integer 0, 1, or 2 (preferably 0 or 1); and geometric isomers or mixtures thereof; and physiologically functional derivatives thereof.

Preferred compound of formula (I) include compound wherein:
$R^1$ represents:
H, $C_{1-4}$alkyl, $C_{3-5}$cycloalkyl;
$R^2$ represents H, $C_{1-4}$alkyl; or
$R^1$ and $R^2$ together form with the nitrogen a 4- or 5-membered heterocyclic ring;
$R^3$ represents I, Cl, Br, F, $CH_3$ or H;
n is an integer 0, 1 or 2.

Preferred compounds of formula (I) include
(a) compounds wherein $R^1$ is cyclopropyl and $R^2$ is H;
(b) compounds wherein either $R^1$ or $R^2$ is H and the other $R^1$ and $R^2$ group is isopropyl;
(c) compounds wherein either $R^1$ or $R^2$ is H and the other $R^1$ or $R^2$ group is tertbutyl;
(d) compounds wherein $R^1$ and $R^2$ together with the nitrogen form an azetidenyl group.
(e) compounds wherein $R^3$ is F and n is 0 or 1;
(f) compounds wherein $R^3$ is $C_{1-4}$alkyl or $C_{2-6}$alkenyl and n is 0 or 1.

It will be appreciated that compounds of formula (I) may exist as geometric ($\alpha$ and $\beta$) isomers and mixtures thereof.

Preferred geometric isomers of the compounds of formula (I) are $1\alpha$, $2\alpha$, $4\beta$ isomers (or, equivalently, $1\beta$, $2\beta$, $4\alpha$ isomers) and $1\alpha$, $2\beta$, $4\alpha$ (or, equivalently, $1\beta$, $2\alpha$, $4\beta$ isomers).

Preferred compounds of formula (I) are:
(1b, 2b, 4a)-4-[5,6-Dichloro-2-(isopropylamino)-1H-benzimidazol-1-yl]-1,2-cyclopentanediol;
(1b, 2b, 4a)-4-[5,6-Dichloro-2-(azetidinyl)1H-benzimidazol-1-yl]-1,2-cyclopentanediol;
(1b, 2b, 4a)-4-[5,6-Dichloro-2-(tert-butylamino)-1H-benzimidazol-1-yl]-1,2-cyclopentanediol;
($1\alpha$, $2\alpha$, $4\beta$)-4-[5,6-Dichloro-2-(cyclopropylamino)-1H-benzimidazol-1-yl]-1,2-cyclopentanediol;
($1\alpha$, $2\beta$, $4\alpha$)-[4-(5,6-Dichloro-2-(isopropylamino)-1H-benzimidazole-1-yl]-2-cyclopentanediol;
($1\alpha$, $2\alpha$, $4\beta$)-[4-(5,6-Dichloro-2-(cyclopropylamino)1H-benzimidazol-1-yl)-1,2-cyclopentylene]dimethanol;
($1\alpha$, $2\alpha$, $4\beta$)-[4-(5,6,-Dichloro-2-(isopropylamino)-1H-benzimidazol-1-yl 1,2-cyclopentylene]dimethanol;
($1\alpha$, $2\alpha$, $4\beta$)-[4-Fluoro-5,6-dichloro-2-(isopropylamino)-1H-benzimidazol-1-yl)-1,2-cyclopentylene]dimethanol;
($1\alpha$, $2\alpha$, $4\beta$)-[4-(5,6-Dichloro-4-iodo-2-(isopropylaminoyl-1H-benzimidazol-1-yl)-1,2-cyclopentane] dimethanol;
($1\alpha$, $2\alpha$, $4\beta$)-[4-(4,5,6-Trichloro-2-(isopropylamine)-1H-benzimidazol-1-yl)-1,2-cyclopentylene]dimethanol;
($1\alpha$, $2\alpha$, $4\beta$)-[4-(5,6-Dichloromethyl-2-(isopropylamino)-1H-benzimidazol-1-yl-1,2-cyclopentylene]dimethanol;
($1\alpha$, $2\alpha$, $4\beta$)-[4-(2-Methyl-1-propenyl)-5,6-dichloro-2-(isopropylamino)-1H-benzimidazol-1-y)-1,2-cyclopentylene]dimethanol;
($1\alpha$, $2\alpha$, $4\beta$)-[4-(2-Methyl-1-propyl)-5,6dichloro-2-(isopropylamino)-1H-benzimidazol-1-yl)-1,2-cyclopentylene]dimethanol;
($\pm$)($1\alpha$, $2\beta$, $4\alpha$)-[4-(5,6-Dichloro-2-(cyclopropylamino)-1H-benzimidazol-1-yl)-1,2-cyclopentylene] dimethanol (including enantiomers thereof); and
($\pm$)-($1\alpha$, $2\beta$, $4\alpha$)-[4-(5,6-Dichloro-2-(isopropylamino)-1H-benzimidazol-1-yl)-1,2-cyclopentylene] dimethanol (including enantiomers thereof).

The invention further includes each possible α and β isomer of the compounds of formula (I) and their physiologically functional derivatives, substantially free of any other geometric isomer(s) that is to say no more than about 5% w/w of the other isomer(s), preferably no more than about 2% w/w, in particular less than 1% w/w will be present. It will be appreciated that in addition to compounds of formula (I) being in a substantially pure form as described above they may also exist as mixtures of enantiomers, diastereoisomers, meso structures or as a racemic mixture. All such geometric isomers are included in the invention as are mixtures of any combination thereof.

As used herein the term "alkyl" means a straight or branched chain alkyl group. Such alkyl groups preferably have 1 to 4 and in particular include methyl, ethyl, i-propyl, and t-butyl.

As used herein, the term "physiologically functional derivative" includes any physiologically acceptable salt, ether, ester, or salt of such ester of a compound of formula (I); or solvates of any thereof; or any other compound which upon administration to the recipient, is capable of providing (directly or indirectly) such a compound or an antivirally active metabolite or residue thereof. For example, it is within the scope of the invention to replace the H of any of the OH groups by a potentially hydrolysable group such as acyl or alkyl.

Preferred esters in accordance with the invention are independently selected from the following groups: (1) carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example, benzyl), aryloxyalkyl (for example, phenoxymethyl), aryl (for example, phenyl optionally substituted by, for example, halogen, $C_{1-4}$alkyl, or $C_{1-4}$alkoxy), or amino; (2) sulphonate esters, such as aryl-, alkyl-, alkylarl or aralkylsulphonyl (for example, toluenesulphonyl and methanesulphonyl); (3) amino acid esters (for example, L-valyl or L-isoleucyl); and (4) phosphonate esters. In such esters, unless otherwise specified, any alkyl moiety present advantageously contains from 1 to 18 carbon atoms, particularly form 1 to 6 carbon atoms, more particularly from 1 to 4 carbon atoms. Any cycloalkyl moiety present in such esters advantageously contains from 3 to 6 carbon atoms. Any aryl moeity present in such esters advantageously comprises a phenyl group. Any reference to any of the above compounds also includes a reference to a physiologically acceptable salt thereof.

Examples of physiologically acceptable salts of compounds of formula (I) and their physiologically acceptable derivatives include salts derived from an appropriate base, such as an alkali metal (for example, sodium), an alkaline earth (for example, magnesium), ammonium and $NX_4^+$ (wherein X is $C_{1-4}$ alkyl). Physiologically acceptable salts of an hydrogen atom or an amino group include salts of organic carboxylic acids such as acetic, lactic, tartaric, maleic, malic, isethionic, lactobionic and succinic acids, organic sulphonic acids, such as methanesulphonic, ethanesulphonic, benzenesulphonic and p-toluenesulphonic acids and inorganic acids, such as hydrochloric, sulphuric, phosphoric and sulphamic acids.

For therapeutic use, salts of compounds of formula (I) will be physiologically acceptable, i.e. they will be salts derived from a physiologically acceptable acid or base. However, salts of acids or bases which are not physiologically acceptable may also find use, for example, in the preparation or purification of a physiologically acceptable compound. All salts, whether or not derived form a physiologically acceptable acid or base, are within the scope of the present invention.

The compounds of formula (I) and their derivatives may hereinafter be referred to as the compounds according to the invention. The term "active ingredient" as used hereafter, unless the context requires otherwise refers to a compound according to the invention.

The present invention further provides a compound according to the invention for use in therapy.

Examples of clinical conditions which may be treated in accordance with the invention include those discussed in the introduction hereinbefore and in particular those caused by infections of HSV-1 and 2, HHV-6, VZV, EBV or CMV.

According to another aspect, the present invention provides:

(a) A method for the treatment or prevention of the symptoms or effects of a viral infection in an infected animal, for example, a mammal including a human, which comprises treating said animal with a therapeutically effective amount of a compound according to the invention. According to a particular embodiment of this aspect of the invention, the viral infection is a herpes virus infection, such as CMV, HSV-1, HSV-2, VZV, EBV or HHV-6.

(b) Use of a compound according to the invention in the manufacture of a medicament for the treatment or prophylaxis of a viral infection, in particular a herpes virus infection including CMV, HSV-1, HSV-2, VZV, EBV and HHV-6.

In addition to the use of compounds of formula (I) in the treatment or prophylaxis of the above viral infections and associated conditions, the compounds may also be used for the treatment or prophylaxis of heart and blood vessel diseases, in particular restenosis and specifically restenosis following angioplasty.

The compounds according to the invention may be administered for therapy by any suitable route including oral, rectal, nasal, topical (including transdermal, buccal and sublingual), vaginal and parenteral (including subcutaneous, intramuscular, intravenous and intradermal). It will be appreciated that the preferred route will vary with the condition and age of the recipient, the nature of the infection and the chosen active ingredient.

In general a suitable dose for each of the above-mentioned conditions will be in the range of 0.01 to 250 mg per kilogram body weight of the recipient (e.g. a human) per day, preferably in the range of 0.1 to 100 mg per kilogram body weight per day and most preferably in the range 1.0 to 20 mg per kilogram body weight per day. (Unless otherwise indicated, all weights of active ingredient are calculated as the parent compound of formula (I); for salts or esters thereof, the weights would be increased proportionally.) The desired dose is preferably presented as two, three, four, five, six or more sub-doses administered at appropriate intervals throughout the day. These sub-doses may be administered in unit dosage forms, for example, containing 10 to 1000 mg, preferably 20 to 500 mg, and most preferably 100 to 400 mg of active ingredient per unit dosage form.

Ideally, the active ingredient should be administered to achieve peak plasma concentrations of the active compound from about 0.025 to about 100 $\mu$M, preferably about 0.1 to 70 $\mu$M, most preferably about 0.25 to 50 $\mu$M. This may be achieved, for example, by the intravenous injection of a 0.1 to 5% solution of the active ingredient, optionally in saline, or orally administered as a bolus containing about 0.1 to about 250 mg/kg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible for the active ingredient to be administered as a raw material it is preferable to present it as a pharmaceutical formulation. The formulations of the present invention comprise at least one active ingredient, as defined above, together with one or more acceptable carriers thereof and optionally other therapeutic agents. Each carrier must be "acceptable" in the sense of being compatible with the other ingredients of the formulation and not injurious to the patient. Formulations include those suitable for oral, rectal, nasal, topical (including transdermal, buccal and sublingual), vaginal or parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research*, 3 (6), 318 (1986).

Formulations of the present invention suitable for oral administration may be presented as discrete units such as capsules, caplets, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multidose sealed containers, for example, ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example, those suitable for oral administration may include such further agents as sweeteners, thickeners and flavoring agents.

The compounds according to the invention may be employed alone or in combination with other therapeutic agents for the treatment of the above infections or conditions. Combination therapies according to the present invention comprise the administration of at least one compound of the formula (I) or a physiologically functional derivative thereof and at least one other physiologically acceptable agent. The active ingredient(s) and physiologically acceptable agents may be administered together or separately and, when administered separately this may occur simultaneously or sequentially in any order. The amounts of the active ingredient(s) and physiologically acceptable agent(s) and the relative timings of administration will be selected in order to achieve the desired combined therapeutic effect. Preferably the combination therapy involves the administration of one compound of the formula (I) or a physiologically functional derivative thereof and one of the agents mentioned herein below.

Examples of such further therapeutic agents include agents that are effective for the treatment of herpes virus infections are acyclovir, penciclovir, famciclovir (the diacetate ester of penciclovir), 2-[(2-amino-1,6-dihydro-6-oxo-9H-purin-9-yl)methoxy]-ethyl L-valinate, phosphonoformic acid and phosphonoacetic acid, ganciclovir, (S)-1-(3-hydroxy-2-phosphonyl methoxypropyl)-cytosine (HPMPC), and Oxetanocin G.

Most preferably the combination therapy involves the joint use of one of the above named agents together with one of the compounds of formula (I) specifically named herein.

The present invention further provides a process for producing a compound of formula (I) or a physiologically functional derivative thereof as hereinbefore defined which process comprises:

A) reacting a compound of formula (II)

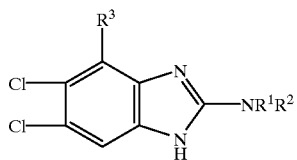

(wherein $R^1$, $R^2$ and $R^3$ are as hereinbefore defined) with a compound of formula (III) or a protected form thereof

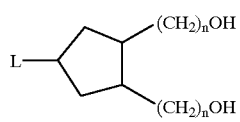

(wherein L is a leaving group and n is hereinbefore defined);
(B) reacting a compound of formula (IV)

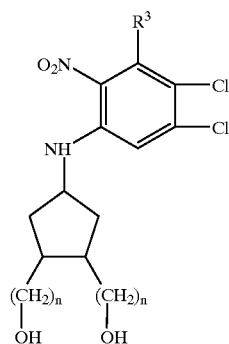

(wherein n and $R^3$ are hereinbefore defined) or a protected form thereof, with a suitable reagent or reagents and/or under conditions serving to convert the compound of formula (IV) into a compound of formula (I);
(C) reacting a compound of formula (V) or a protected form thereof

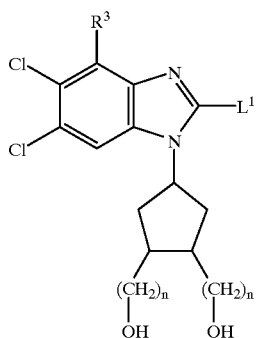

(wherein $L^1$ is a leaving group preferable a halo group such as Cl, Br, F and I, and $R^3$ and n are hereinbefore defined);
(D) reacting a compound of formula (I) or (V) or a protected form of either (wherein compounds (I) and (V) are hereinbefore defined and wherein $R^3$ represents H) with an alkyl lithium base and subsequently reacting the intermediate with an electrophilic agent selected to effect the change of $R^3$ (wherein $R^3$ is hereinbefore defined) to any group other than H.

Preferably in step (D) the initial reaction with the alkyl lithium base (preferably sec-butyllithium) is carried out at low temperature (preferably at below −20° C.) with protected forms of the compounds of formula (I) or (V). The secondary stage of converting the intermediate species to compounds of formula (I) is effected using a suitable electrophile to produce the desired $R^3$ group, for example, $C_{1-4}$alkyl or $C_{2-6}$alkenyl halides, carbon dioxide, halogenating reagents or carbonyl compounds. Such steps may be carried out in accordance with the procedures described in V. Snieckus, Chem. Rev., 1990, vol. 90, page 879–933.

Preferred protecting groups are silyl protecting groups, preferably t-butyldimethyl silyl.

Compounds of formula (III) may be prepared in accordance with the procedures described in Depres & Greene, J. Org. Chem. 1962, 27:2395–2398.

Compounds of formula (IV) may be prepared by reacting a compound of formula (III) with 1,2,4trichloro-5-nitrobenzene (commercially available Aldrich).

Compounds of formula (V) may be prepared by reacting a compound of formula (VI)

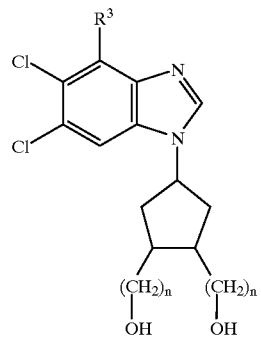

(wherein R3 is hereinbefore described) with N-halo succinimide (commercially available, Aldrich).

The intermediates of formula (V) were also found to have antiviral activity and represent a further feature of the invention, preferable wherein $L^1$ is Br.

The following examples are intended for illustration only and are not intended to limit the scope of the invention in any way. The term "active ingredients" as used in the examples means a compound of formula (I) or a physiologically functional derivative thereof.

EXAMPLE 1

(1α, 2α, 4α)-[4(2-Bromo-5,6-dichloro-1H-benzimidazol-1-yl)-1,2-cyclopentylene]dimethanol a) (1α, 2α, 4α)-1,2-Dimethanol cyclopentane-4-ol To a 3 L flask equipped with an overhead mechanical stirrer, 500 mL addition funnel, low temperature thermometer and nitrogen inlet, was added 1 M lithium aluminum hydride in tetrahydrofuran (Aldrich Sure Seal, 1.1 L) using a canula. The solution was stirred and cooled (dry icetacetone bath) to 10° C. (internal temperature) and a solution of cis-dimethyl4oxo-1,2-cyclopentanedicarboxylate (68.0 g, 0.340 mol) (Gais et al., J. Org. Chem 1989, 54:5115–5122) in tetrahydrofuran (Mallinckrodt, 500 mL) was added dropwise so that the internal temperature did not rise above 0° C. (ca. 2 h). The cooling bath was removed and the reaction was allowed to warm to room temperature and stirred two hours.

Sodium fluoride (Aldrich 99%, 289 g) was added in several portions, and the resulting slurry was stirred 1 hour at room temperature and then cooled to 0° C. (NaCl/ice bath) as a solution of water (205 mL) in tetrahydrofuran (500 mL) was added so that an internal temperature of 0° C. was maintained. After the addition was complete (ca. 3 hours), the reaction was allowed to warm to room temperature and stirred for 1 hour. The slurry was suction-filtered and the filter plug was broken up and stirred in 20:4:1 tetrahydrofuran-methanol-water (1500 mL) until the solids were free-flowing, then suction-filtered again. This process was repeated with additional 1:1 methanol-tetrahydrofuran (1 L) and the combined filtrates were concentrated under reduced pressure, co-evaporating with absolute ethanol to a viscous oil. The oil was dissolved in 5:1 chloroform-methanol (500 mL) and suction-filtered through a plug of flash silica gel, eluting with additional solvent (ca. 500 mL) until tlc of the filtrates on silica gel plates developed in 10% methanol-chloroform and visualized with phosphomolybdic acid reagent (20% in ethanol, Aldrich) showed no product. The combined filtrates were concentrated under reduced pressure, co-evaporating with absolute ethanol, affording the title compound as a colorless syrup (50.5 g, 97%); $^1$H-NMR (DMSO-$d_6$, 200 MHz)δ: 4.58 (m, 3, 3 OH), 4.01 (m, 1, CHOH), 3.53 and 3.38 (both m, 2 each, 2CH$_2$OH), 2.01, 1.86, 1.22 (each m, each 2, cyclopentyl CH), contains ca. 4% of the 4b-isomer by integration of multiplet at 4.11 (3 OH).

Anal. Calcd. for $C_7H_{14}O_3 \cdot 0.35$ $H_2O$: C, 55.14; H, 9.72. Found: C, 55.02; H, 9.78.

b) (5a'-α, 8a'-α, 7'-β)-Hexahydrospiro(cyclohexene-1,3'-1H-cyclopenta[e][1,3] dioxepin)7-ol Freshly distilled cyclohexanone (Aldrich, 400 mL) was added to a 1 L flask containing (1α, 2α, 4α)-1,2-dimethanol cyclopentane-4-ol (Part a, 16.9 g, 0.116 mmol), p-toluenesulfonic acid monohydrate (0.045 g, 0.236 mmol, Aldrich, 99%) and 20 g of 4 Å molecular sieves (Davidson, 8–12 mesh, pre-dried at 800° C.). The mixture was stoppered and vigorously stirred at room temperature for 24 hours at which point tlc on silica gel plates developed with 10% methanol-chloroform indicated completion. Sodium bicarbonate (0.044 g, 0.525 mmol) and chloroform (300 mL) were added and the mixture was suction-filtered through a plug of flash silica gel, washing with additional chloroform (500 mL). The solvents were evaporated under reduced pressure and the residual solid was recrystallized from hexanes-ethyl acetate, affording the title compound as a white solid (22.53 g, 86%), m.p. 92–95° C.

Anal. Calcd. for $C_{13}H_{22}O_3$: C, 68.99; H, 9.80. Found: C, 69.14; H, 9.89.

c) (5'-α, 7'-α, 8a'-α)Hexahydrospiro(cyclohexene-1,3'-1H-cyclopentate[e][1,3]dioxepin)-7-ol To a stirred solution of (5a'-α, 8a'-α, 7'-β)-hexahydrospiro (cyclohexene-1,3'-1H-cyclopenta[e][1,3]dioxepin)-7-ol (Part b, 22.5 g, 99.4 mmol), triphenylphosphine (Aldrich, 27.7 g, 104 mmol as 99%) and glacial acetic acid (6.00 mL, 104 mmol) at 0° C., under nitrogen was added dropwise diethyl azodicarboxylate (Aldrich, 16.9 mL, 104 mmol as 97%) over a 0.5 hour period. The resulting slurry was allowed to warm to room temperature, stirred an additional 2 hours, then placed in the refrigerator overnight. Triphenyl phosphine oxide and diethylhydrazine dicarboxylate were removed by suction-filtration. The filtrate was diluted with 10:1 hexanes-ethyl acetate and washed with saturated aqueous sodium bicarbonate. Concentration and addition of more hexanes precipitated the remaining Mitsunobu byproducts. The filtrates were suction-filtered through a plug of flash silica gel 60 (230–400 mesh), eluting product with 20% ethyl acetate-hexanes. Volatiles were evaporated and the residual oil was dissolved in 1:1 tetrahydrofuran-methanol (200 mL) and stirred with 1 N aqueous sodium hydroxide (50 mL) overnight at room temperature. The reaction mixture was diluted with water, extracted with chloroform, and the combined organic layers dried (sodium sulfate), filtered, and concentrated. Recrystallization from hexanes-ethyl acetate gave the title compound as white needles (17.2 g, 76%), m.p. 110° C.

Anal. Calcd. for $C_{13}H_{22}O_3$: C, 68.99; H, 9.80. Found: C, 69.02; H, 9.79.

d) (1α, 2α, 4α)-[4-(5,6-dichloro-1H-benzimidazol-1-yl)-1.2-cyclopentylene]dimethanol (5a'-α, 7'-α8a'-α)-Hexahydrospiro(cyclohexene-1,3'-1H-cyclopenta[e][1,3]dioxepin)-7-ol (Part c, 3.00 g, 13.3 mmol), triphenylphosphine (Aldrich, 4.17 g, 15.9 mmol, as 99%), 5,6-dichlorobenzimidazole (Townsend and Revankar, Chem. Rev 1970, 70:389, and references cited therein) (2.98 g, 15.9 mmol) were stirred in anhydrous tetrahydrofuran (Aldrich Sure Seal, 80 mL) at 0° C. (external ice bath) under nitrogen as a solution of diethyl azodicarboxylate (Aldrich, 2.50 mL, 15.9 mmol as 97%) in tetrahydrofuran (20 mL) was added over 30 min. The reaction was allowed to warm to room temperature, stirred 36 hours, then diluted with chloroform (500 mL) and washed with 0.1 N aqueous sodium hydroxide (100 mL). The organic layer was dned (sodium sulfate), filtered, and the solvents evaporated under reduced pressure. The residual gum was dissolved in tetrahydrofuran (200 mL) with 0.1 N HCl (20 mL) and stirred at room temperature for 72 hours at which point tlc on silica plates developed with 10% methanol-chloroform indicated the presence of ca. 10% starting material. An additional 20 mL of 0.1 N hydrochloric acid was added and stirrng continued for 24 h. The pH was then adjusted to 6–7 with 1 N sodium hydroxide and the solution was concentrated under reduced pressure, coevaporating with ethanol, affording a solid which was purified by flash chromatography on silica gel 60. The title compound was eluted with 5–25% methanol-chloroform as a white solid (3.17 g, 76%), m.p. 192–195° C.

Anal. Calcd. for $C_{14}H_{16}N_2O_2Cl_2$: C, 53.35; H, 5.12, N, 8.89, Cl, 22.50. Found: C, 53.49; H, 5.09, N, 8.83, Cl, 22.57.

e) (1α, 2α, 4α)-[4-(2-Bromo-5,6dichloro-1H-benzimidazol-1-yl)-1,2-cyclopentylene]dimethyl Diacetate To a stirred solution of (1α, 2α, 4α)-[4-(5,6-dichloro-1H-benzimidazol-1-yl)-1,2-cyclopentylene]dimethanol (Part d, 2.90 g, 9.20 mmol) in anhydrous pyridine (100 mL) was added acetic anhydride (4.30 mL, 46.0 mmol). After 12 hours the reaction mixture was concentrated under reduced pressure, coevaporating with toluene to a viscous oil. Ethanol (ca. 5 mL) was added (with external ice cooling) and the mixture was again coevaporated with tolune (2x) until acetic acid odor was absent. The oil was redissolved in chloroform (200 mL) and washed successively with 0.1 N HCl (50 mL), saturated aqueous sodium bicarbonate (50 mL), and brine (50 mL). The organic layer was dried (sodium sulfate) then suction-filtered through a plug (3×4 cm) of flash silica gel 60, washing with 5% methanol-chloroform (200 mL). Evaporation of the solvents under reduced pressure left a light brown gum (3.92 g) which was dissolved in anhydrous tetrahydrofuran (Aldrich Sure Seal, 70 mL), heated to reflux under nitrogen with stirring, and N-bromosuccinimide (Aldrich, 3.28 g, 18.4 mmol) was added in one portion. After 10 min. at reflux, tlc on silica gel plates developed with 2% methanol-chloroform indicated the reaction was complete. The yellow solution was cooled to room temperature, diluted with chloroform (500 mL) and washed with saturated aqueous sodium bicarbonate (3×100 mL). The organic layer was dried (sodium sulfate), filtered, and concentrated under reduced pressure, providing a brown gum which was purified by flash chromatography on silica gel 60. The title compound eluted with 50% ethyl acetate-hexanes as an off-white solid (3.22 g, 75%) which was chromatographically homogeneous by tlc and had $^1$H-NMR identical with that described below. Such a sample was recrystallized from absolute ethanol, affording title compound as a white crystalline solid, m.p. 107–109° C.; mass spectrum (Cl/CH$_4$) 476.9 (63%), 478.9 (100%), 480.9 (49%); $^1$H-NMR (CDCl$_3$, 200 MHz)δ:8.07, 7.97 (both s, 1 each, benzimidazole CH), 5.04 (m, 1, CHN), 4.23 (m, 4, 2CH$_2$OAc), 2.61 (m, 2, cyclopentyl CH), 2.21 (m, 4, cyclopentyl CH), 2.08 (s, 6, 2OAc).

Anal. Calcd. for $C_{18}H_{19}BrCl_2N_2O_4$: C, 45.21; H, 4.01, N, 5.86, Br, 16.71, Cl, 14.83. Found: C, 45.3; H, 4.03, N, 5.91, Br, 16.66, Cl, 14.79.

f) (1α, 2α, 4α)-[4-(2-Bromo-5,6-dichloro-1H-benzimidazol-1-yl)-1,2-cyclopentylene]dimethanol (1α, 2α, 4α)-[4-(2-Bromo-5,6-dichloro-1H-benzimidazol-1-yl)-1,2-cyclopentylene]dimethyl diacetate (Part e, 2.90 g, 6.06 mmol) was dissolved in 1:1 methanol-ethanol (200 mL). A solution of sodium carbonate (640 mg, 6.06 mmol) in water (40 mL) was added and the reaction mixture was stirred 5 hours at room temperature. The pH was then adjusted to 5 with glacial acetic acid and the solvents evaporated in vacuo. The residual solid was slurried in water until the solids were freeflowing, then suction-filtered and dried overnight in vacuo affording the title compound as a white solid (2.27 g, 98%), m.p. 190–195° C.; mass spectrum (Cl/CH$_4$):392.8 (60%), 394.8 (100%), 396.8 (46%); $^1$H-NMR (CDCl$_3$, 200 MHz)d: 8.44, 8.41 (both s, 1 each, benzimidazole CH), 4.98 (m, 1, CHN), 4.98 (bs. 2, 2OH), 3.68 (m, 4, 2CH$_2$OH), 2.30–1.95 (m, 6 H cyclopentyl CH).

Anal. Calcd. for $C_{14}H_{15}BrCl_2N_2O_2$: C, 42.67; H, 3.84, N, 7.11, Br, 20.28, Cl, 17.99. Found: C, 42.74; H, 3.91, N, 7.10, Br, 20.23, Cl, 17.95.

EXAMPLE 2

(1α, 2α, 4α)-[4-(5,6-Dichloro-2-(cyclopropylamino)-1H-benzimidazol-1-yl)-1,2-cyclopentylene]dimethanol A solution of (1α, 2α, 4α)-[4-(2-bromo-5,6-dichloro-1H-benzimidazol-1-yl)1,2-cyclopentylene]dimethanol (Example 1, 500 mg, 1.27 mmol) and cyclopropyl amine (Aldrich, 4.30 mL, 6.34 mmol) in absolute ethanol (20 mL) was refuxed under nitrogen for 4 days at which point tlc (silica gel plates developed with 5% methanol-chloroform) indicated complete conversion to lower Rf product. 1 N sodium hydroxide (1.3 mL) was added and the reaction mixture was concentrated under reduced pressure. The residual solids were chromatographed on silica gel 60. Title compound was eluted with 10% methanol-chloroform as a white foam, after evaporation of solvents (370 mg, 79%), m.p. 190–200° C.; mass spectrum (Cl/CH$_4$): 370.0 (100%), 372 (67%); $^1$H-NMR (CDCl$_3$, 200 MHz)δ: 7.79, 7.44 (both s, 1 each, benzimidazole CH), 7.25 (bs, 1, NH), 4.91 (t, J=4.3 Hz, 2OH), 4.71 (m, 1, CHN), 3.68 (m, 4, 2CH$_2$OH), 2.78 (m, 1, NCH-c-Pr), 2.21–1.95 (m, 6, cyclopentyl CH), 0.73 (m, 2, c-Pr H), 0.56 (m, 2, c-Pr H).

Anal. Calcd. for $C_{17}H_{21}Cl_2N_3O_2$: C, 55.14; H, 5.72, N. 11.35, Cl, 19.15. Found: C, 55.01; H, 5.83, N, 11.14, Cl, 19.02.

EXAMPLE 3

(1α, 2α, 4β)-[4-(2-Bromo-5,6-dichloro-1H-benzimidazol-1-yl)-1,2-cyclopentylene]dimethanol a) (1α, 2α, 4β)-[4-(5,6-Dichloro-1H-benzimidazol-1-yl)-1,2-cyclopentylene]dimethanol Mitsunobu reaction (Mitsunobu, *Synthesis* 1981, 1–28), deblocking, and purification were carried out as in Example 1, part d, using(5a'-α, 8a'-α, 7'-β)-hexahydrospiro (cyclohexene-1,3'-1H-cyclopenta[e][1,3]dioxepin)-7-ol (Example 1, part b, 3.21 g, 14.2 mmol), triphenylphosphine (Aldrich, 4.51 g, 17.01 mmol as 99%), 5,6-dichlorobenzimidazole (Townsend and Revankar, *Chem. Rev.* 1970, 70, 389, and references cited therein) (3.18 g, 17.01 mmol) in anhydrous tetrahydrofuran (60 mL) and a solution of diethyl azodicarboxylate (Aldrich, 2.80 mL, 17.01 mmol as 97%) in tetrahydrofuran (20 mL). Title compound was obtained as a white solid (2.58 g, 63%), m.p. 163° C.

Anal. Calcd. for $C_{14}H_{16}N_2O_2Cl_2$: C, 53.35; H. 5.12, N, 8.89, Cl, 22.50. Found: C, 53.36; H, 5.19, N, 8.81, Cl, 22.40.

b) (1α, 2α, 4β)-[4-(2-Bromo-5,6-dichloro-1H-benzimidazol-1-yl)-1,2-cylopentylene]dimethyl Diacetate Acetylation, bromination, and purification was carried out as in Example 1, part e, starting with (1α, 2α, 4β)-[4-(5,6-dichloro-1H-benzimidazol-1-yl)-1,2-cyclopentylene] dimethanol (Part a of this example, 2.50 g, 7.93 mmol), acetic anhydride (3.70 mL, 40.0 mmol) in pyridine (50 mL), then N-bromosuccinimide (2.82 g, 15.83 mmol) in tetrahydrofuran (70 mL), providing the title compound as a white solid (3.30 g, 87%), m.p. 125–130_C.; $^1$H-NMR (CDCl$_3$, 200 MHz) δ: 7.99, 7.96 (both s, 1 each, benzimidazole CH), 5.36 (m, 1, CHN), 4.12 (apparent d, J=6.1 Hz, 4, 2CH$_2$OAc), 2.88 (m, 2, 2CHCH$_2$OAc), 2.41–2.04 (m, 4, cyclopentyl CH), 2.07 (s, 6, 2OAc).

Anal. Calcd. for $C_{18}H_{19}BrCl_2N_2O_4$: C, 45.21; H, 4.01, N, 5.86, Br, 16.71, Cl, 14.83. Found: C, 45.15; H, 4.14, N, 5.74, Br, 16.63, Cl, 14.83.

c) (1α, 2α, 4β)-[4-(2-Bromo-5,6-dichloro-1H-benzimidazol-1-yl)-1,2-cyclopentylene]dimethanol Deblocking and purification was carried out as in Example 1, part f, starting with (1α, 2α, 4β)-[4-(2-bromo-5,6-dichloro-1H-benzimidazol-1-yl)-1,2-cyclopentylene] dimethyl diacetate (Part b of this example, 3.15 g, 6.59 mmol) in 1:1 methanol-ethanol (260 mL) and a solution of sodium carbonate (0.70 g, 6.59 mmol) in water (40 mL) and 1 hour reaction time, to provide the title compound (2.23 g, 86%), m.p. 155–162° C.; $^1$H-NMR (CDCl$_3$, 200 MHz) δ: 7.97, 7.88 (both S, 1 each, benzimidazole CH), 5.39 (m, 1, CHN), 4.65 (bt, J~1 Hz, 2, 2OH), 3.54 (m, 4, 2CH$_2$OH), 2.63–2.10 (m, 6, cyclopentyl CH).

Anal. Calcd. for $C_{14}H_{15}BrCl_2N_2O_2$·0.60 H$_2$O: C, 41.16; H, 4.10, N, 6.86, Br, 17.36, Cl, 19.56. Found: C, 41.18; H, 4.04, N, 6.87, Br, 17.38, Cl, 19.59.

EXAMPLE 4

(1α, 2α, 4β)-[4-(5,6-Dichloro-2-(cyclopropylamino)-1H-benzimidazol-1-yl)-1,2-cyclo pentylene]dimethanol A solution of (1α, 2α, 4β)-[4-(2-bromo-5,6-dichloro-1H-benzimidazol-1-yl)-1,2-cyclopentylene]dimethanol (Example 3, part c, 500 mg, 1.22 mmol) in cyclopropyl amine (10 mL) was stirred and heated (80° C., external bath) in a Parr bomb for 12 hours. 1 N sodium hydroxide (1.22 mL) was added, the solvents removed under reduced pressure, and the resulting solid purified by flash chromatography on silica gel 60. Elution with 2–10% methanol-chloroform gave an off-white foam which was slurried in ethanol-water and suction-filtered, providing the title compound as a white solid (360 mg, 80%), m.p. 215° C.; mass spectrum (Cl/CH$_4$): 370.0 (100%), 372.0 (69%); $^1$H-NMR (CDCl$_3$, 200 MHz)δ: 7.49, 7.29 (both s, I each, benzimidazole CH), 7.19 (bs, 1, NH), 4.89 (m, 1, CHN), 4.56 (bt, J=4.9 Hz, 2, 2OH), 3.57–3.38 (m, 4, 2C$_2$OH), 2.76 (m, 1, NCH-c-Pr), 2.01 (m, 6, cyclopentyl CH), 0.73 (m, 2, c-Pr H), 0.56 (m, 2, c-Pr H).

Anal. Calcd. for C$_{17}$H$_{21}$Cl$_2$N$_3$O$_2$: C, 55.14; H, 5.72, N, 11.35, Cl, 19.15. Found: C,55.37; H, 5.81, N, 11.12, Cl, 18.87.

EXAMPLE 5

(1α, 2α, 4β)-[4-(5,6-Dichloro-2-(isopropylamino)-1H-benzimidazol-1-yl)-1,2-cyclo pentylene]dimethanol (1α, 2α, 4β)-[4-(2-Bromo-5,6-dichloro-1H-benzimidazol-1-yl)-1,2-cyclopentylene]dimethanol (Example 3, part c, 600 mg, 1.47 mmol), isopropyl amine (1.80 mL, 21.9 mmol, Fluka) in absolute ethanol (5 mL) was refluxed 3 days. An additional 1.80 mL of isopropyl amine was added and refluxing continued for 24 hours. 1 N sodium hydroxide (1.50 mL) was added, the reaction was concentrated under reduced pressure and the residual solid purified by flash chromatography on silica gel 60. Elution with 10% methanol-chloroform and evaporation of solvent gave a solid foam which was slurried in water, then suction-filtered to give the title compound as a white solid (430 mg, 79%), m.p. 206–209° C.; $^1$H-NMR (CDCl$_3$, 200 MHz)δ: 7.40, 7.26 (both s, 1, benzimidazole CH), 6.67 (bd, J=7.5 Hz, 1, NH), 4.97 (m, 1, CHN), 4.58 (t, J=5.1 Hz, 2, 2OH), 4.03 (m, 1 H, CHNCHMe$_2$), 3.59–3.39 (m, 4, 2CH$_2$OH), 2.02 (m, 6, cyclopentyl CH), 1.24 (d, J=6.6 Hz, 6, 2Me).

Anal. Calcd. for C$_{17}$H$_{23}$Cl$_2$N$_3$O$_3$: C, 54.85, H, 6.23, N, 11.29, Cl, 19.05. Found: C, 54.77, H, 6.20, N, 11.21, Cl, 18.97.

EXAMPLE 6

(1α, 2α, 4β)-4-(2-Bromo-5,6-Dichloro-1H-benzimidazol-1-yl)-1,2-cyclopentanediol a) Benzyl N-(3-cyclopenten-1-yl)carbamate A solution of 3-cyclopentene-1-carboxylic acid (Depres and Greene, J. Org. Chem. 1962, 27:2395–2398) (30.5 g, 0.272 mole) in dry benzene (360 mL) was stirred while a solution of diphenylphosphoryl azide (Aldrich, 74.85 g, 0.272 mole as 97%) and triethylamine (41.7 mL, 0.299 mole) in benzene (130 mL) was added over 20 minutes. The solution was refluxed for 2 hours and then benzyl alcohol (32.4 mL, 0.313 mole) was added. The solution was refluxed for 20 hours, cooled, and concentrated in vacuo to a brown oil. A solution of the oil in ethyl acetate (600 mL) was washed with 0.5 N hydrochloric acid (300 mL), then water (2×350 mL), then saturated aqueous sodium bicarbonate (300 mL), and dried (sodium sulfate). Evaporation left title compound as white solid (41.0 g, 69%), $^1$H-NMR consistent with structure. Recrystallization of such a sample from ethyl acetate-hexanes gave benzyl N-(3-cyclopenten-1-yl) carbamate as colorless waxy crystals, m.p. 56–57° C.

Anal. Calcd for C$_{13}$H$_{15}$NO$_2$: C, 71.87; H, 6.96; N, 6.45. Found: C, 71.79; H, 6.94; N6.8.

b) (1β, 3α, 4β)-Benzyl N-(3,4-dihydroxy-1-cyclopentyl) carbamate and (1-a, 3-a, 4a)-Benzyl N-(3,4-dihydroxy-1-cyclopentyl)carbamate A solution of benzyl N-(3-cyclopenten-1-yl)carbamate (Example 6, part a, 28.0 g, 0.128 mole), N-methyl morpholine N-oxide (Aldrich, 25.1 mL of 60% aqueous solution, 0.145 mole), and osmium tetroxide (Aldrich, 2.6 mL of 2.5% solution in t-butanol) in acetone (350 mL) was refluxed for 8 hours. An additional 2.6 mL of the osmium tetroxide solution was added and reflux continued for 5 hours. The solution was concentrated in vacuo and the residual oil was chromatographed on silica gel. Elution with 10% methanol-chloroform gave fractions containing (1-β, 3-α, 4α)-benzyl N-(3,4-dihydroxy-1-cyclopentyl)carbamate as a white solid (9.2 g, 28%), m.p. 136–138° C.

Anal. Calcd for C$_{13}$H$_{17}$NO$_4$·0.20H$_2$O: C, 61.26; H. 6.88; N, 5.50. Found: C, 61.26; H, 6.67; N, 5.56.

Continued elution of the column gave fractions containing a mixture of title compounds (4.0 g, 12%) followed by fractions containing pure (1α, 3α, 4β)-benzyl N-(3,4-dihydroxy-1-cyclopentyl)carbamate as white solid (7.50 g, 23%), m.p. 105–107° C.

Anal. Calcd for C$_{13}$H$_{17}$NO$_4$: C, 62.15; H, 6.82; N, 5.58. Found: C, 61.98; H. 6.97; N, 5.51.

c) (1α, 2α, 4β)-4-(4,5-Dichloro-2-nitroanilino)1,2-cyclopentanediyl Diacetate

A solution of (1β, 3α, 4β)-benzyl N-(3,4-dihydroxy-1-cyclopentyl)carbamate (Example 6, part b, 11.0 g, 43.8 mmol) in acetic acid (250 mL) was shaken with 10% palladium on carbon (1 g) under hydrogen (45 psi) on a Parr shaker for 1.25 hours at ambient temperature. The catalyst was filtered off (Celite) and volatiles evaporated in vacuo. The residual oil was dissolved in dry dioxane (100 mL)-N, N-dimethylformamide (15 mL) and refluxed with anhydrous potassium carbonate powder (24.2 g, 0.175 mole as 98%) and 1,2,4-trichloro-5-nitrobenzene (Aldrich, 10.17 g., 43.8 mmol as 97%) for 4 days under nitrogen atmosphere. Solids were filtered off and the filtrate was concentrated in vacuo to a red oil. The oil was stirred with pyridine (100 mL)-acetic anhydride (11 mL) at ambient temperature for 24 hours. Volatiles were evaporated and the residue dissolved in chloroform. The chloroform solution was washed with saturated aqueous sodium bicarbonate, then saturated aqueous sodium chloride, and dried (sodium sulfate). Evaporation of volatiles gave title compound as a yellow solid (10.8 g, 63%). Such a sample, after elution from a silica gel column with chloroform gave title compound as yellow crystals, m.p. 164–166° C.

Anal. Calcd for C$_{15}$H$_{16}$N$_2$O$_6$Cl$_2$: C, 46.05; H, 4.12; N, 7.16; Cl, 18.12. Found: C, 45.98; H, 4.16; N, 7.08; Cl, 18.16.

d) (1α, 2α, 4β)-4-(2-Bromo-5,6-dichloro-1H-benzimidazo-1l-yl)-1,2-cyclopentanediyl Diacetate A mixture of (1α, 2α, 4β)-4-(4,5dichloro-2-nitroanilino)-1,2-cyclopentanediyl diacetate (Example 6, part c, 10.8 g, 27.6 mmol), iron powder (Fisher electrolytic, 94.5%, 7.71 g, 138 mequiv), and ferrous sulfate heptahydrate (Aldrich, 3.84 g, 13.8 mequiv) in 3:1 ethanol-water (300 mL) was refluxed with stirring for 1.5 hours. Solids were filtered off and the filtrate concentrated in vacuo to a brown oil. A solution of the oil in chloroform (125 mL) was refluxed with triethylorthoformate (6.9 mL, 41.4 mmol) and methanesulfonic acid (0.18 mL, 2.76 mmol) for 1.0 hour. The cooled solution was washed with saturated aqueous sodium bicarbonate (75 mL) and dried (sodium sulfate). Volatiles were evaporated in vacuo and the residual oil was dissolved in dry tetrahydrofuran (150 mL) and refluxed while solid N-bromosuccinimide (Aldrich, 9.82 g, 52.2 mmole) was added in one portion. Reflux was continued for 20 minutes. The cooled solution was diluted with chloroform (200 mL) and washed with saturated aqueous sodium bicarbonate (75 mL), then water (3×75 mL), and dried (sodium sulfate). Volatiles were evaporated in vacuo and the residual solid was chromatographed on silica gel. Title compound was eluted with 1% methanol-chloroform as a white solid, crystallized from ethyl acetate-hexanes (6.73 g, 54%), $^1$H-NMR in DMSO-d6 consistent with structure. Recrystallization of such a sample from ethanol gave (1α, 2α, 4β)-4-(2-bromo-5,6-dichloro-1H-benzimidazol-1-yl)-1,2-cyclopentanediyl diacetate as white crystals, m.p. 180–182° C.

Anal. Calcd for $C_{16}H_{15}N_2O_4Cl_2Br$ C, 42.69; H, 3.36; N, 6.22; total halogen as Cl, 23.63. Found: C, 42.86; H, 3.43; N, 6.15; total halogen as Cl, 23.53.

e) (1α, 2α, 4β)-4-(2-Bromo-5,6-dichloro-1H-benzimidazol-1-yl)-1,2-cyclopentanediol (1α, 2α, 4β)-4-(2-Bromo-5,6-chloro-1H-benzimidazol-1-yl)-1,2-cyclopentanediyl diacetate (Example 6, part d, 640 mg, 1.42 mmol) was added to a mixture of sodium carbonate (150 mg) and 1:4:4 water-methanol-ethanol (27 mL) and the mixture stirred for 1.25 hours at ambient temperature. Volatiles were evaporated in vacuo after neutralization with glacial acetic acid. The residual solids were recrystallized from ethanol-water to give (1α, 2α, 4β)-4-(2-bromo-5,6-dichloro-1H-benzimidazol-1-yl)-1,2-cyclopentanediol as white crystals (340 mg, 65%), m.p. 100–105 °C.; $^1$H-NMR (DMSO-d6)δ: 7.96 and 7.89 (both s, 1 each, 2 aromatic CH), 5.4–5.3 (m, 1, NCH), 4.84 (d, J=4.3 Hz, 2, 2 OH), 4.4–4.3 (m, 2, 2 OCH), 2.36–2.00 (two m, 4,2 $CH_2$).

Anal. Calcd for $C_{12}H_{11}N_2O_2Cl_2Br$: C, 39.38; H, 3.03; N, 7.65; total halogen as Cl, 29.06. Found: C, 39.20; H, 3.17; N, 7.56; total halogen as Cl, 28.95.

EXAMPLE 7

(1α, 2α, 4β)-4-[5,6-Dichloro-2-(cyclopropylamino)-1H-benzimidazol-1-yl]-1,2-cyclopentanediol A solution of (1α, 2α, 4β)-4-(2-bromo-5,6-dichloro-1H-benzimidazol-1-yl)-1,2-cyclopentanediyl diacetate (Example 6, part d, 600 mg, 1.33 mmol) and cyclopropylamino (Aldrich, 0.92 mL, 13.3 mmol) in absolute ethanol (10 mL) was refluxed 36 hours. An additional 0.47 mL of cyclopropylamino was added and reflux continued for 16 hours. 1 N sodium hydroxide (1.3 mL) was added to the cooled solution and volatiles were evaporated in vacuo. The residual tan oil was chromatographed on silica gel. The title compound eluted with 5% methanol-chloroform as white crystals, after crystallization from ethyl acetate-hexanes (352 mg, 77%), m.p. 235–236° C.; $^1$H-NMR (DMSO-d6)δ: 7.47 and 7.25 (both s, 1 each, 2 aromatic CH), 7.30 (d, J=2.1 Hz, 1, NH), 5.15–4.90 (m, 1, NCH), 4.75 (d, J=3.5 Hz, 2, 2OH), 4.3–4.2 (m, 2, 2OCH), 2.8–2.7 (m, 1, CH), 2.2–1.85 (m, 4, 2$CH_2$), 0.8–0.5 (m, 4, cyclopropyl).

Anal. Calcd for $C_{15}H_{17}N_3O_2Cl_2$: C, 52.65; H, 5.01; N, 12.28; Cl, 20.72. Found: C, 52.69; H, 5.09; N, 12.22; Cl, 20.80.

EXAMPLE 8

(1α, 2α, 4β)-4-[5,6-Dichloro-2-(isopropylamino)-1H-benzimidazol-1-yl]-1,2-cyclopentanediol A solution of (1α, 2α, 4β)-4(2-bromo 5,6-dichloro-1H-benzimidazol-1-yl)-1,2-cyclopentanediyl diacetate (Example 6, part d, 550 mg, 1.22 mmol) and isopropylamine (Fluka, 1.04 mL, 12.2 mmol) in 2-methoxyethanol (15 mL) was refluxed for 8 hours. 1 N sodium hydroxide (1.2 mL) was added to the cooled solution and the volatiles were evaporated in vacuo. The residual oil was chromatographed on silica gel. Title compound eluted with 15% methanol-chloroform as white crystals, after crystallization from ethyl acetate-hexanes (270 mg, 64%), m.p. 200–201 °C.; $^1$H-NMR (DMSO-d6)δ: 7.39 and 7.21 (both s, 1 each, 2 aromatic CH), 6.84 (d, J=7.6 Hz, 1, NH), 5.2–5.0 (m, 1, NCH), 4.75 (m, 2, 2OH), 4.3–4.2 (m, 2, 2OCH), 4.1–3.9 (m, 1, CHNH), 2.2–1.9 (m, 4, 2$CH_2$), 1.22 (d, J=6.4 Hz, 6, 2Me).

Anal. Calcd for $C_{15}H_{19}N_{3O2}Cl_2$: C, 52.33; H, 5.56; N, 12.21; Cl, 20.60. Found: C, 52.28; H, 5.54; N, 12.11; Cl, 20.53.

EXAMPLE 9

(1α, 2α, 4β)-4-[5,6-Dichloro-2-(azetidinyl)-1H-benzimidazol-1-yl]-1,2-cyclopentanediol A solution of (1α, 2α, 4β)-4-(2-bromo-5,6-dichloro-1H-benzimidazol-1-yl)-1,2-cyclopentanediol (Example 6, part e, 350 mg, 0.95 mmol) and azetidine (Aldrich, 250 mg, 4.4 mmol as 98%) in absolute ethanol (15 mL) was refluxed for 45 minutes. 1 N sodium hydroxide (1.0 mL) was added to the cooled solution and the volatiles were evaporated in vacuo. Crystallization of the residual solid from ethanol gave title compound as white crystals (245 mg, 75%), m.p. 247–249 °C.; $^1$H-NMR (DMSO-d6)δ: 7.56 and 7.42 (both s, 1 each, 2 aromatic CH), 5.0–4.2 (m, 3, NCH and 2OH), 4.3–4.2 (m, 2, 2OCH), 4.18 (t, J=7.6 Hz, 4, 2$CH_2$N), 2.45–1.8 (m, 6, 3$CH_2$).

Anal. Calcd for $C_{15}H_{17}N_3O_2Cl_2$: C, 52.65; H. 5.01; N, 12.28; Cl, 20.72. Found: C, 52.83; H, 5.19; N, 12.09; Cl, 20.62.

EXAMPLE 10

(1α, 2α, 4β)-4-[5,6-Dichloro-2-(tert-butylamino)-1H-benzimidazol-1-yl]-1,2-cyclopentanediol A solution of (1α, 2α, 4β)-4-(2-bromo-5,6-dichloro-1H-benzimidazol-1-yl)-1,2-cyclopentanediyl diacetate (Example 6, part d, 750 mg, 2.00 mmol) in tert-butylamine (Aldrich, 10 mL) was heated with stirring in a Parr bomb at 150_C. for 3 days. 1 N sodium hydroxide (2.0 mL) was added to the cooled solution and the volatiles were evaporated in vacuo. The residual brown oil was chromatographed on silica gel. Title compound eluted with ethyl acetate as white crystals, after crystallization from ethanol-water (380 mg, 49%), m.p. 113–116° C.; $^1$H-NMR (DMSO-d6)δ: 7.44 and 7.23 (both s, 1 each, 2 aromatic CH), 6.39 (s, 1, NH), 5.25–5.05 (m, 1, NCH), 4.75 (d, J=3.7 Hz, 2, 2OH), 4.3–4.2 (m, 2, 2OCH), 2.2–1.9 (m, 4, 2$CH_2$), 1.46 (s, 9, 3Me).

Anal. Calcd for $C_{16}H_{21}N_3O_2Cl_2 \cdot 1.5 H_2O$: C, 49.88; H, 6.28; N, 10.91; Cl, 18.40. Found: C, 50.04; H, 6.31; N, 10.82; Cl, 18.17.

EXAMPLE 11

(1α, 2α, 4β)-4-[5,6-Dichloro-2-(isopropylamino)-1H-benzimidazol-1-yl]-1,2-cyclopentanediol a) (1α, 2α, 4α)-4-(4,5-Dichloro-2-nitroanilino)-1,2-cyclopentanediol A solution of (1α, 3α, 4β)-benzyl N-(3,4-dihydroxy-1-cyclopentyl)carbamate (Example 6, part b, 7.30 g, 29.1 mmol) in ethanol (250 mL) was shaken with 10% palladium on carbon (750 mg) under hydrogen (45 psi) on a Parr shaker for 5.0 hours at ambient temperature. The catalyst was filtered off (Celite) and volatiles evaporated in vacuo. The residual oil was dissolved in dry dioxane (100 mL)-N,N-dimethylformamide (10 mL) and refluxed with anhydrous potassium carbonate powder (12.0 g, 87.2 mmole as 98%) and 1,2,4-trichloro-5-nitrobenzene (Aldrich, 6.78 g., 29.1 mmol as 97%) for 3 days under nitrogen atmosphere. Solids were filtered off and the filtrate was concentrated in vacuo to a red oil. The oil was chromatographed on silica gel. The compound was eluted with 10% methanol-chloroform as yellow solid (4.80 g, 53%). Such a sample was recrystallized from ethyl acetate to give title compound as yellow crystals, m.p. 137–139_° C.

Anal. Calcd for $C_{11}H_{12}N_2O_4Cl_2$: C, 43.02; H, 3.94; N, 9.12; Cl, 23.09. Found: C, 43.21; H, 4.01; N, 8.99; Cl, 22.95.

b) (1α, 2α, 4α)-4-(2-Bromo-5,6-dichloro-1H-benzimidazol-1-yl)-1,2-cyclopentanediy Diacetate A mixture of (1α, 2α, 4α)-4-(4,5-dichloro-2-nitroanilino)-1,2-cyclopentanediol (Part a of this example, 4.55 g, 14.8 mmol), iron powder (Fisher electrolytic, 94.5%, 4.36 g, 74.1 mequiv), and ferrous sulfate heptahydrate (Aldrich, 2.00 g, 7.40 mequiv) in 3:1 ethanol-water (300 mL) with 3 drops of concentrated aqueous hydrochloric acid was refluxed with stirring for 3.0 hours. Solids were filtered off and the filtrate concentrated in vacuo to a brown oil. A solution of the oil in chloroform (50 mL) was refluxed with triethylorthoformate (19.6 mL, 118 mmol) and methanesulfonic acid (0.10 mL, 1.50 mmol) for 1.5 hours. Volatiles were evaporated in vacuo and the residual oil was dissolved 1 N hydrochloric acid (50 mL) and stirred at ambient temperature for 1.0 hour. The solution was neutralized with 1 N sodium hydroxide, volatiles evaporated and the residue dissolved in 5% methanol-chloroform and filtered through silica gel. The filtrate was concentrated to a tan solid which was stirred in pyridine (50 mL)-acetic anhydride (4 mL) at ambient temperature for 24 hours. Volatiles were evaporated in vacuo. The residual oil was dissolved in chloroform. The chloroform solution was washed with saturated aqueous sodium bicarbonate, then water, and dried (sodium sulfate). Evaporation of volatiles left an oil which was dissolved in tetrahydrofuran (25 mL) and brought to reflux. N-bromosuccinimide (2.91 g, 60.1 mmol) was added to the refluxing solution in one portion. Reflux was continued for 10 minutes. Workup as in Example 6, part d, afforded the title compound as white crystals (2.58 g, 38%), m.p. 205–207° C.

Anal. Calcd for $C_{16}H_{15}N_2O_4Cl_2Br$: C, 42.69; H, 3.36; N, 6.22; total halogen as Cl, 23.63. Found: C, 42.63; H, 3.30; N, 6.16; total halogen as Cl, 23.66.

c) (1α, 2α, 4α)-4-[5,6-Dichloro-2-(isoprodamino)-1H-benzimidazol-1-yl)-1,2-cyclopentanediol A solution of (1α, 2α, 4α)-4-(2-bromo-5,6-dichloro-1H-benzimidazol-1-yl)-1,2-cyclopentanediyl diacetate (Part b of this example, 600 mg, 1.33 mmol) was converted to title compound by the procedure of Example 8. Crystallization from ethanol-water gave title compound as white crystals (200 mg, 44%), m.p. 228–230° C.; $^1$H-NMR (DMSO-$d_6$)δ: 7.78 and 7.35 (both s, 1 each, 2 aromatic CH), 7.28 (d, J=7.3 Hz, 1, NH), 5.34 (d, J=3.7 Hz, 2, 2OH), 5.0–4.8 (m, 1,CHNH), 4.0–3.8 (m, 3, 2OCH and NCH), 2.3–2.1 and 2.05–1.9 (both m, 4, 2CHS), 1.24 (d, J=6.5 Hz, 6, 2Me).

Anal. Calcd for $C_{15}H_{19}N_3O_2Cl_2$·0.25 $H_2O$: C, 51.66 H, 5.64; N, 12.05; Cl, 20.33. Found: C, 51.52; H, 5.45; N, 11.84; Cl, 20.44.

EXAMPLE 12

(±)-(1α, 2β, 4α)-[4-(2-Bromo-5,6-dichloro-1H-benzimidazol-1-yl)-1,2-cyclopentylene]dimethyl Dipivalate a) (±)-(1α, 2β, 4α)-1,2-Dimethanol cyclopentane-4-ol By the method of Example 1, part a, (±)-trans-dimethyl-4-oxo-1,2-cyclopentanedicarboxylate (Legraverend et al., *Heterocycles* 1991, 32: 1785–1792; 8.40 g, 41.9 mmol) was reduced to give title compound as an off-white solid (5.80 g, 95%), after solidification from ethyl acetate-methanol; m.p. 57–59° C.

Anal. Calcd. for $C_7H_{14}O_3$: C, 57.51; H, 9.65. Found: C, 57.29; H, 9.56.

b) (±)-(1α, 2β, 4α)-[4-(5,6-Dichloro-1H-benzimidazol-1-yl)-1,2-yclopentylene]dimethyl Dipivalate A solution of (±)-(1α, 2β, 4α)-1,2-Dimethanol cyclopentane-4-ol (part a of this example, 5.40 g, 17.18 mmol) and pyridine (21 mL, 130 mmol) in inithvlcne chloride (50 mL) was cooled (brine/ice bath) and trimethylacetyl chloride (8.10 mL, 65.13 mmol) was added over 20 minutes. The solution was stirred 30 minutes, diluted with ethyl acetate (500 mL) and washed with 0.1 N HCl (500 mL) then water (200 mL). The organic layer was dried (sodium sulfate), filtered, concentrated in vacuo, providing an oil which was purified by chromatography on silica gel 60. Elution with 10 % ethyl acetate-hexanes removed undesired (±)-(1α, 2β, 4α)-[4-(5,6-Dichloro-1H-benzimidazole-1-yl)-1,2-cyclopentylene]dimethyl tripivalate (2.50 g). Continued elution with 50% ethyl acetate-hexanes gave (±)-(1α, 2β, 4α)-(4-hydroxy-1,2-cyclopentylene)dimethyl dipivalate as an oil (5.40 g, 50%) which was reacted with 5,6-dichlorobenzimidazole (Townsend and Revankar, *Chem. Rev.* 1970, 70, 389, and references cited therein) (3.85 g, 20.6 mmol) as described in example 1, part d. The residual oil was chromatographed on silica gel eluting with 50% ethyl acetate-hexanes. Concentration gave the title compound along with 30% hydrazine diethyl dicarboxyate (NMR) which was removed by dissolving the mixture in diethyl ether (200 mL) and washing with water (5×25 mL). The organic phase was dried (sodium sulfate), concentrated in vacuo and the oil solidified from hexanes affording the title compound (5.25 g, 63%) as a white solid. Concentration of the filtrates and reprecipitation gave additional title compound (1.40 g, 17%), m.p. 117–119 ° C.

Anal. Calcd for $C_{24}H_{32}N_2O_4Cl_2$: C, 59.63; H, 6.67; N, 5.79; Cl, 14.67. Found: C, 59.78; H, 6.71; N. 5.78; Cl, 14.46.

c) (±)(1α, 2β, 4α)-[4-(2-Bromo-5,6-dichloro-1H-benzimidazol-1-yl)-1,2-cyclopentylene]dimethyl Dipivalate By the method of Example 1, part e, (±)(1α, 2β, 4α)-[4-(5,6-dichloro-1H-benzimidazol-1-yl)-1,2-cyclopentylene] dimethyl dipivalate (Part b of this example, 5.07 g, 10.5 mmol) was brominated. Trituration of the crude product in hexanes gave the title compound as an off-white solid (4.99 g, 85%), m.p. 129–130° C.

Anal. Calcd for $C_{24}H_{31}N_2O_4BrCl_2$: C, 51.26; H, 5.56; N, 4.98; Br, 14.21; Cl, 12.61. Found: C, 51.18; H, 5.57; N, 5.03; Br, 14.20; Cl, 12.60.

EXAMPLE 13

(±)-(1α, 2β, 4α)-[4-(5,6-Dichloro-2-(cyclopropvlaminol)-1H-benzimidazol-1-yl)-1,2-cyclopentylene]dimethanol a) (±)-(1α, 2β, 4α)-[4-(5,6-Dichloro-2-(cyclopropylamino)-1H-benzimidazol-1-yl) 1,2-cyclopentylene]dimethyl Dipivalate A solution of (±)-(1α, 2β, 4α)-[4-(2-Bromo-5,6dichloro-1H-benzimidazol-1-yl)-2-cyclopentylene]dimethyl dipivalate (Example 12, part c, 1.50 g, 2.67 mmol), cyclopropyl amine (9.0 mL, 50 mmol) in absolute EtOH (20 mL) was refluxed under nitrogen for 1 day. The yellow solution was diluted with ethyl acetate (200 mL), washed with dilute sodium bicarbonate (2×50 mL), and the organic phase was dried (sodium sulfate), then concentrated in vacuo. The residual solid was triturated in 20% ethyl acetate-hexanes affording the title compound as a white crystalline solid (1.31 g, 94%), m.p. 92–94° C.

Anal. Calcd for $C_{27}H_{37}N_3O_4Cl_2$: C, 60.22; H. 6.93; N, 7.80; Cl, 13.17. Found: C, 60.27; H, 6.98; N, 7.70; Cl, 13.15.

b) (±)-(1α, 2β, 4α)-[4-(5,6-Dichloro-2-(cyclopropylamino)-1H-benzimidazol-1-yl)-1,2-cyclopentylene]dimethanol (±)-(1α, 2β, 4α)-[4-(5,6-Dichloro-2-(cyclopropylamino)-1H-benzimidazol-1-yl)-1,2-cyclopentylene]dimethyl dipivalate (part a of this example, 1.20 g, 2.23 mmol) was refuxed in 0.5 N NaOH (40 mL) and ethanol (20 mL) for 2 hours. The yellow solution was adjusted to pH 7 with 1 N NaOH, concentrated to dryness, and purified by silica get chromatography. Elution with 10% methanol-chloroform gave 0.702 g of the trimethylacetic acid salt of title compound. This solid was dissolved in ethanol (20 mL), then passed through a 3×1 cm column of Amberlite IRA-400 (OH- form) ion-exchange resin (Aldrich) with ethanol (50 mL). Concentration and trituration in water gave the title compound (0.260 g, 31 %) as an off-white solid, m.p. 229–231° C.; $^1$H-NMR (DMSO-d$_6$)δ: 7.50, 7.46 (both s, each 1, benzimidazole H), 7.20 (bs, 1, NH), 4.83 (t, J=4.9 Hz, 1, OH), 4.68 (t, J=5 Hz, 1, OH), 4.68 (m, 1, CHN), 3.57–3.33 (m, 4, 2CH$_2$OH), 2.76 (m, 1, CHc-Pr), 2.29–1.76 (m, 6, cyclopentyl H), 0.74, 0.56 (each m, each 1, c-Pr CB$_2$).

Anal. Calcd for C$_{17}$H$_{21}$N$_3$O$_2$Cl$_2$·0.10 EtOH·0.05 H$_2$O: C, 54.98; H, 5.82; N, 11.18; Cl, 18.87. Found: C, 54.95; H, 5.90; N, 11.09; Cl, 18.91.

EXAMPLE 14

(±)-(1α, 2β, 4α)-[4-(5,6-Dichloro-2-(isopropylamino)-1H-benzimidazol-1-yl)-1,2-cylopentylene]dimethanol a) (±)-(1α, 2β, 4α)-[4-(5,6-Dichloro-2-(isopropylamino)-1H-benzimidazol-1-yl) 1,2-cyclopentylene]dimethyl Dipivalate By the method of part a of Example 13, (±)-(1α, 2β, 4α)-[4-(2-Bromo-5,6-dichloro-1H-benzimidazol-1-yl)-1,2-cyclopentylene]dimethyl dipivalate (part c of Example 12, 1.00 g, 1.78 mmol)) was reacted with isopropyl amine affording the title compound, after solidification from ethyl acetate-hexanes, as a white solid (0.95 g, 98%), m.p. 140–145° C.

Anal. Calcd for C$_{27}$H$_{39}$N$_3$O$_4$Cl$_2$: C, 60.00; H, 7.27; N, 7.77; Cl, 13.12. Found: C, 59.81; H, 7.26; N, 7.73; Cl, 13.19.

b) (±)(1α, 2β, 4α)-[4-(5,6-Dichloro-2-(isopropylamino)-1H-benzimidazol-1-yl)-1,2-cyclopentylene]dimethanol (±)-(1α, 2β, 4α)-[4-(5,6-Dichloro-2-(isopropylamino)-1H-benzimidazol-1-yl)-1,2-cyclopentylene]dimethyl dipivalate (part a of this example, 0.84 g, 1.70 mmol) was refuxed in 0.5 N NaOH (40 mL) and ethanol (30 mL) for 2 hours. The colorless solution was acidified to pH 1 by adding 1 N HCl ( ca. 20 mL) and co-evaporated with water (3×). The title compound was isolated as its hydrochloride salt, after filtration and washing with water, as a white solid (0.60 g, 78%), m.p. 175–180° C.; $^1$H-NMR (DMSO-d$_6$)δ: 8.66 (brs, 1, NH), 7.86, 7.63 (both s, each 1, benzimidazole H), 5.01 (m, 1, CHN), 4.02 (m, 1, CHMe$_2$), 3.59–3.35 (m, 4, 2CH$_2$OH), 2.35–1.87 (m, 6, cyclopentyl H), 1.32 (d, J=6.2 Hz, 2, 2Me).

Anal. Calcd for C$_{17}$H$_{23}$N$_3$O$_2$Cl$_2$·1.0 HCl·1:0 H$_2$O: C, 47.64; H, 6.16; N, 9.80; Cl, 24.82. Found: C, 47.76; H, 6.45; N, 9.66; Cl, 24.57.

EXAMPLE 15

(1α, 2α, 4β)-[4-(5,6-Dichloro-4-iodo-2-(isopropylamino)-1H-benzimidazol-1-yl)-1,2-cyclopentylene]dimethanol a) (5a'-α, 8a'-α, 7'-β)-Hexahydrospiro(cyclohexene-1,3'-1H-cyclopenta[e][1,3]dioxepin)-7-yl methanesulfonate A solution of (5a'-α, 8a'-α, 7'-β)-Hexahydrospiro (cyclohexene-1,3'-1H-cyclopenta[e][1,3]dioxepin)7-ol (Example 1, part b, 10.5 g, 46.4 mmol) and triethylamine (9.7 mL, 65 mmol) in anhydrous methylene chloride (200 mL) was cooled (ice bath), with stirring, as methanesulphonyl chloride (4.0 mL, 51 mmol, as 98%) was added dropwise over 10 minutes. After 15 minutes, the slurry was washed sequentially with ice-cooled portions (100 mL each) of water, 0.5 N HCl and brine. The organic layer was dried (sodium sulfate) and suction-filtered through a plug of silica gel (2×5 cm), eluting with ethyl acetate (2×50 mL). Concentration provided a colorless oil which solidified upon standing affording the title compound as a white crystalline solid (14.07 g, 99%), m.p. 90–94° C.

Anal. Calcd for C$_{14}$H$_{24}$O$_5$S: C, 55.24; H, 7.95; S, 10.53. Found: C, 55.12; H, 7.99; S, 10.59.

b) (6a'-α, 8a'-α, 7'-α)-5,6-Dichloro-1-[hexahydrospiro (cyclohexene-1,3'-1H-cyclopenta[e][1,3]dioxepin)-7'-yl]-2-(isopropylamino)-1H-benzimidazole To a stirring solution of 5,6-dichloro-2-isopropylamino-benzimidazole (PCT Application No. GB95.01597, 10.3 g, 42.2 mmol) in anhydrous tetrahydrofuran (200 mL), under nitrogen, was added potassium tert-butoxide (Aldrich, 40 mL, as 1 M in tetrahydrofuran). The brown solution was heated to 60° C. for 30 minutes and (5a'-α, 8a'-α, 7'-β)-hexahydrospiro(cyclohexene-1,3'-1H-cyclopenta[e][1,3] dioxepin)7-yl methanesulfonate (part a of this example, 12.9 g, 42.2 mmol) in tetrahydrofuran (50 mL) was added in one portion (syringe). The reaction mixture was stirred 24 h, diluted with chloroform (500 mL) and washed with water (2×100 mL). The organic extracts were dried (sodium sulfate) and concentrated in vacuo to a brown solid which was chromatographed on silica gel. The title compound eluted with 10–50% ethyl acetate-hexanes as an off-white foam (16.6 g, 82%), m.p. 157–159° C.

Anal. Calcd for C$_{23}$H$_{31}$N$_3$Cl$_2$O$_2$: C, 55.24; H, 7.95; S, 10.53. Found: C, 55.12; H, 7.99; S, 10.59.

c) (1α, 2α, 4β)-[4-(5,6-Dichloro-4-iodo-2-(isopropylamino-1H-benzimidazol-1-yl)1,2-cyclopentylene]dimethanol To a stirring solution of (6a'-α, 8a'-α, 7'-α)-5,6dichloro-1-[hexahydrospiro(cyclohexene-1,3'-1H-cyclopenta[e][1,3]dioxepin)-7'-yl]-2-(isopropylaminoyl)-1H-benzimidazole (part b of this example, 1.00 g, 2.21 mmol) in anhydrous tetrahydrofuran (15 mL) under nitrogen at −78° C. (dry icetacetone) was added dropwise sec-butyl lithium (Aldrich, 8.6 mL, as 0.90 M in hexane) over 5 minutes. The resulting yellow slurry was stirred 1 hour and a solution of iodine (1.75 g, 7.74 mmol) in tetrahydrofuran (1 mL) was added. The reaction was poured into saturated aqueous sodium hydrogen carbonate (100 mL) and extracted with chloroform (2×100 mL). The combined organic extracts were washed with a dilute solution of aqueous sodium thiosulfate (50 mL), dried (sodium sulfate), and concentrated to dryness. Purification by chromatography on silica gel 60, eluting with 10–50% ethyl acetate-hexanes provided a chromatographically homogeneous white solid (0.79 g, 62%) whose $^1$H-NMR and mass spectrum were consistent with structure. Deblocking was carried out by stirring in tetrahydrofuran (10 mL) and 1 N HCl (1.5 mL) for 12 h. The title compound was obtained as a white solid after suction-filtration, washing with water, and drying (0.44 g, 55%), m.p. 238–241 ° C. dec.; $^1$H-NMR (DMSO-d$_6$)δ: 8.20 (bs, 1, NH), 7.42 (s, 1, aromatic CH), 5.16 (m, 1, NCH), 5.20–4.00 (brd, 3, 2 OH and 1HCl), 4.30 (m, 1, NCH-i-Pr), 3.62–3.37 (m, 4, 2 CH$_2$OH), 2.52 (m, 2, CH), 2.05 (m, 4, CH), 1.31 (d, J=6.4 Hz, 6,2 Me).

Anal. Calcd for C$_{17}$H$_{22}$N$_3$O$_2$Cl$_2$I ·1.0 HCl·1.0 H$_2$O: C, 36.95 H, 4.56; N, 7.60; Cl, 19.24, I, 22.96. Found: C, 36.98; H, 4.50; N, 7.60; Cl, 19.24, 1, 22.90.

EXAMPLE 16

(1α, 2α, 4β)-[4-(5,6-Dichloro-4-bromo-2-(isopropylamino)-1H-benzimidazol-1-yl)-1,2-cyclopentylene]dimethanol By the method of Example 15, part c, (6a'-α, 8a'-α, 7'-α)-5,6-dichloro-1-[hexahydrospiro(cyclohexene-1,3'-1H-cyclopenta[e][1,3]dioxepin)-7'-yl]-2-(isopropylamino)-1H-benzimidazole (1.0 g, 2.21 mmol) was lithiated and quenched at −78° C. with bromine (ca. 0.3 mL) until color persisted. Workup and purification as described provided the title compound as a hygroscopic salt which was neutralized with 1 N NaOH in methanol. Concentration, trituration in water, and drying provided the title compound as a white solid (0.29 g, 35% overall), m.p. 195–198_C.; $^1$H-NMR (DMSO-d$_6$)δ: 7.30 (s, 1, aromatic CH), 6.87 (bd, J=7.6 Hz, 1, NH), 4.98 (m, 1, NCH), 4.59 (bs, 2, 2OH), 4.16 (m, 1, NCH-i- Pr), 3.54–3.35 (m, 4, 2 CH$_2$OH), 2.02 (m, 6, CH), 1.26 (d, J=6.4 Hz, 6, 2 Me).

Anal. Calcd for C$_{17}$H$_{22}$N$_3$O$_2$Cl$_2$Br C, 45.25 H, 4.91; N, 9.31; Cl, 15.72, Br, 17.71. Found: C, 45.28; H, 4.96; N, 9.22; Cl, 15.67, Br, 17.67.

EXAMPLE 17

(1α, 2α, 4β)-[4,5,6-Trichloro-2-(isopropylamino)-1H-benzimidazol-1-yl)-1 2-cyclo pentylene]dimethanol By the method of Example 15, part c, (6a'-α, 8a'-α, 7'-α)-5,6-Dichloro-1-[hexahydrospiro(cyclohexene-1,3'-1H-cyclopenta[e][1,3]dioxepin)-7'-yl]-2-(isopropylamino)-1H-benzimidazole (1.0 g, 2.21 mmol) was lithiated then treated at −78° C. with hexachloroethane (0.50 g). Workup and purification as described gave the title compound as a white hydrochloride salt (0.35 g, 40% overall), m.p. 184–186° C.; $^1$H-NMR (DMSO-d$_6$)δ: 8.27 (bs, 1, NH), 7.42 (s, 1, aromatic CH), 5.20 (m, 1, NCH), 4.80–4.00 (brd, 2OH and 1HCl), 4.24 (m, 1, NCH-i-Pr), 3.60–3.30 (m, 4, 2 CH$_2$OH), 2.00 (m, 6, CH), 1.31 (d, J=6.4 Hz, 6, 2 Me).

Anal. Calcd for C$_{17}$H$_{22}$N$_3$O$_2$Cl$_3$·1.0 HCl ·1.2 H$_2$O: C, 43.93 H, 5.51; N, 9.04; Cl, 30.51. Found: C, 43.99; H, 5.86; N, 8.98; Cl, 30.74.

EXAMPLE 18

(1α, 2α, 4β)-[4-(5,6-Dichloro-4-methyl-2-(isopropylamino)-1H-benzimidazol-1-yl)-1,2-cyclopentylene]dimethanol (1α, 2α, 4β)-[4-(5,6-Dichloro-2-(isopropylaminoy-1H-benzimidazol-1-yl)-1,2-cyclo pentylene]dimethanol (Example 5, 1.10 g, 3.31 mmol) in anhydrous N,N-dimethyl formamide (10 mL) was treated with imidazole (0.71 g, 10.0 mmol) then tert-butyldimethylsilyl chloride (1.10 g, 6.94 mmol, as 97%). After 15 minutes methanol was added and volatiles removed in vacuo. The residual solid was purified by chromatography on silica gel, eluting with 5–20% ethyl acetate-hexanes, affording a brittle foam (1.50 g, 85%) which was homogeneous by tic and showed NMR and mass spectrum consistent with structure. A solution of this compound in anhydrous tetrahydrofuran (15 mL) was stirred at −78° C. (dry ice/acetone) and treated dropwise with sec-butyl lithium (Aldrich, 8.9 mL, as 0.90 M in hexane) over 5 minutes. The resulting slurry was stirred 1 hour, treated with methyl iodide (0.5 mL) for 15 minutes, then quenched with 1 N HCl (8.0 mL) and allowed to warm to room temperature. The mixture was extracted with chloroform (50 mL) and the organic extracts dried (sodium sulfate), and concentrated to dryness. Purification on silica gel by eluting with 5–50% ethyl acetate-hexanes gave a chromatographically homogeneous brown oil (1.48 g, 96%) which showed NMR and mass spectrum consistent with structure. Desilylation was accomplished by stirring in tetrahydrofuran (25 mL) and 1 N hydrochloric acid (2.5 mL) for 24 hours. The neutralized solution (1 N sodium hydroxide) was concentrated and purified by chromatography on silica gel. The title compound eluted with 10% methanol-ethyl acetate as a white solid (0.55 g, 61%), m.p. 160–162° C.; $^1$H-NMR (DMSO-d$_6$)δ:7.15 (s, 1, aromatic CH), 6.55 (bd, J=7.4 Hz, 1, NH), 4.96 (m, 1, NCH), 4.58 (t, J=5 Hz, 2, 2OH), 4.13 (m, 1, NCH-i-Pr), 3.56–3.39 (m, 4, 2 CH$_2$OH), 2.47 (s, 3, Me), 2.50 (m, 2, CH), 2.01 (m, 4, CH), 1.25 (d, J=6.4 Hz, 6, 2 Me).

Anal. Calcd for C$_{18}$H$_{25}$N$_3$O$_2$Cl$_2$: C, 55.96 H, 6.52; N, 10.88; Cl, 18.35. Found: C, 55.87; H, 6.52; N, 10.84; Cl, 18.39.

EXAMPLE 19

(±)-(1α, 2β, 4α)-4-(5,6-Dichloro-2-(isopropylamino)-1H-benzimidazol-1-yl)-1,2-cyclopentanediol a) tert-Butyl N-(3-cyclopenten-1-yl)carbamate To a solution of 3-cyclopentene-1-carboxylic acid (J.-P. Depres and A. E. Greene, J. Org. Chem. 1984, 49:928–931; 29.71 g, 0.261 mole), triethylamine (36.4 mL) in t-butanol (1 L) was added diphenylphosphoryl azide, Aldrich, 97%, 74.0 g, 0.261 mmole). The solution was maintained at 60_C. for 4 hours. Cuprous chloride (1.3 g) was added and stirring continued at ambient temperature for 18 hours. Volatiles were evaporated and the residue was dissolved in methylene chloride (1250 mL) and washed with 10 % aqueous sodium carbonate (2×250 mL) and dried (magnesium sulfate). Volatiles were evaporated and the residue was chromatographed on a silica gel column. Title compound was eluted with chloroform as white crystals, from hexanes (22.63 g, 47%), m.p. 68–70° C.

Anal. Calcd for C$_{10}$H$_{17}$NO$_2$: C, 65.54 H, 9.35; N, 7.64. Found: C, 65.53; H, 9.40; N, 7.59.

b) (±)-(1α, 2β, 4α)-4-(4,5-Dichloro-2-nitroanilino)-1,2-cyclopentanediol

To a cooled (ice bath) mixture of m-chloroperbenzoic acic (Aldrich, 80%, 12.98g, 60.1 mmol) in methylene chloride (110 mL) was added a solution of tert-butyl N-(3-cyclopenten-1-yl)carbamate (11.0 g, 60.1 mmol) in methylene chloride (110 mL). The mixture was stirred at ambient temperature for 18 hours. Additional m-chloroperbenzoic acid (120 mg) was added and stirring continued for 2 hours. The solid was filtered off, washed with methylene chloride (25 mL), and the combined filtrate-wash stirred with anhydrous calcium hydroxide (Aldrich, 98%, 4.53 g, 60.1 mmol) for 4 hours. The solids were removed by filtration and the filtrated was concentrated to a white waxy solid. This solid was dissolved in 1 N aqueous sulfuric acid (120 mL)—dioxane (20 mL) and the solution was maintained at 60° C. for 3.5 hours. The resulting solution was cooled, concentrated to 60 mL in vacuo, and washed through Amberlite IRA-400 (OH form) ion exchange resin (500 mL). Elution with water (800 mL) and evaporation of the water in vacuo left (±)(1α, 2β, 4α)-4-amino-1,2-cyclopentanediol as a colorless oil (6.04 g, 87%), $^1$H- NMR (DMSO-d$_6$) consistent with structure. This oil was converted to the title compound by methods described in Example 6, part c. Crude product was eluted from a silica gel pad with 10% methanol-chloroform and crystallized from ethyl acetate-methanol to provide title compound as yellow crystals (6.34 g, 34%), m.p. 154–156° C.

Anal. Calcd for C$_{11}$H$_{12}$N$_2$O$_2$Cl$_2$: C, 43.02; H, 3.94; N, 9.12; Cl, 23.09. Found: C, 43.08; H, 3.97; N, 9.07; Cl, 22.99.

c) (±)-(1α, 2β, 4α)-4-(5,6-Dichloro-1H-benzimidazol-1-yl)-1,2-cyclopentanediyl Diacetate (±)(1α, 2β, 4α)-4-(4,5-Dichloro-2-nitroanilino)-1,2-cyclopentanediol (part b of this example, 7.00 g, 22.8 mmol) was converted to tide compound by the methods of Example 6. Title compound eluted from a silica gel column in 5% methanol-chloroform as a tan oil (4.68 g,55%).

Anal Calcd for C$_{16}$H$_{16}$N$_2$O$_4$Cl$_2$·0.05 EtOAc·0.25 H$_2$O: C, 51.19; H, 4.48; N, 7.37; Cl, 18.65. Found: C, 51.12; H, 4.46; N, 7.42; Cl, 18.78.

d) (±)-(1α, 2β, 4α)-4-(2-Bromo-5,6-dichloro-1H-benzimidazol-1-yl)-1,2-cyclopentanediyl Diacetate (±)-(1α, 2β, 4α)-4-(5,6-Dichloro-1H-benzimidazol-1-yl)-1,2-cyclopentanediyl diacetate (part c of this example, 4.62 g, 12.5 mmol) was brominated by the method of Example 6, part d, to give tide compound as a white solid after solidification from ethyl acetate (4.06 g, 73% ), m.p. 151–152° C.

Anal. Calcd for C$_{16}$H$_{15}$N$_2$O$_4$Cl$_2$Br. C, 42.70; H, 3.36; N, 6.22; total halogen as Cl, 18.05. Found: C, 42.73; H, 3.39; N, 6.15; total halogen as Cl, 23.60.

e) (±)-(1α, 2β, 4α)-4-(2-Bromo-5,6dichloro-1H-benzimidazol-1-yl)-1,2-cyclopentanediol (±)-(1α, 2β, 4α)-4-(2-Bromo-5,6-dichloro-1H-benzimidazol-1-yl)-1,2-cyclopentanediyl diacetate (part c of this example, 2.00 g, 4.44 mmol) was converted by the method of Example 6, part e, to give title compound as a white solid, after solidification from water (1.33 g, 82%), m.p. 230–235° C. dec. $^1$H-NMR (DMSO-d$_6$)δ: 8.92, and 7.96 (both s, 1 each, 2 aromatic CH), 5,61 (d, J=2.6 Hz, 1, OH), 5.40–5.20 (m, 1 NCH ), 5.11 (d, J=2.2 Hz,1, OH), 4.1–4.0 (m, 2, 2OCH), 2.70–2.30 (m, overlaping solvent, 2CH), 2.05–1.85 (m, 2, 2CH).

Anal. Calcd for $C_{12}H_{11}N_2O_2Cl_2Br$: C, 39.38; H, 3.03; N, 7.65; total halogen as Cl, 29.06. Found: C, 39.43; H, 3.07; N, 7.59; total halogen as Cl, 29.03.

EXAMPLE 20

(±)-(1α, 2β, 4α)-4-(5,6-dichloro-2-(isopropylamino)-1H-benzimidazol-1-yl)1,2-cyclopentanediol A solution of (±)-(1α, 2β, 4α)-4-(2-Bromo-5,6-dichloro-1H-benzimidazol-1-yl1)-1,2-cyclopentanediol (Example 19, part e, 400 mg, 1.09 mmol) and isopropylamine (Fluka,0.92 mL,10.9 mmol) in ethanol (10 mL)-methoxy ethanol (5 mL) was refluxed 24 hours. Additional isopropyl amine (1.84 mL) was added and reflux continued for an additional 48 hours. 1 N sodium hydroxide (1.1 mL) was added to the cooled solution and the volatiles removed in vacuo. The residual white solid was chromatographed on silica gel. Elution with 10% methanol-chloroform gave (±)(1α, 2β, 4α)-4-(5,6-dichloro-2-(isopropylamino)-1H-benzimidazol-1-yl)-1,2-cyclopentane-diol isolated as a white solid from water (294 mg, 77%), m.p. 198–200_C. $^1$H-NMR (DMSO-d$_6$)δ: 7.84, and 7.36 (both s, 1 each, 2 aromatic CH), 7.17 (d, j=2.5 Hz, 1, NH), 5.82 (d, J=2.5 Hz, 1, OH), 5.20–5.00 (m, 1 NCH), 4.99 (d, J=2.5 Hz, 1, OH), 4.10–3.95 (m, 3, 2OCH and CHNH), 2.60–2.40 (m, overlaping solvent, 2CH), 1.22 (d, J=6.5 Hz, 6, 2CH$_3$)

Anal. Calcd for $C_{15}H_{19}N_3O_2Cl_2Br·0.3H_2O$: C, 51.53; H, 5.65; N, 12.02; total halogen as Cl, 20.28. Found: C, 51.45; H, 5.61; N, 12.02; total halogen as Cl, 20.28.

EXAMPLE 21

(1α, 2α, 4β)-[4-(4-Dimethylcarboxamide-5,6-dichloro-2-(isopropylamino)-1H-benzimidazol-1-yl)-1,2-cyclopentylene]dimethanol By the method of Example 15, part c, (6a'-α, 8a'-α, 7'-α)-5,6-dichloro-1-[hexahydrospiro(cyclohexene-1,3'-1H-cyclopenta[e][1,3]dioxepin)-7'-yl ]-2-(isopropylamino)-1H-benzimidazole (1.0 g, 2.21 mmol) was lithiated then treated at −78° C. with dimethylcarbamoyl chloride (0.35 mL, 3.80 mmol). After 0.5 h the reaction was neutralized with 1 N HCl to pH 7, then partitioned with ethyl acetate and water. The organic layers were dried (sodium sulfate). Concentration and precipitation from ethyl acetate gave the blocked intermediate as a white solid (0.94 g) which was carried directly onto deprotection as previously described using 1 N HCl (1.5 mL) and tetrahydrofuran (15 mL). The neutralized solution (1 N NaOH) was concentrated and purified by chromatography on silica gel. The title compound eluted with 10% methanol-chloroform as a white foam (0.42 g, 71% overall), m.p. >250° C., decomp.; $^1$H-NMR (DMSO-d$_6$)δ: 7.29 (s, 1, aromatic CH), 6.74 (d, J=7.6 Hz, 1, NH), 5.20 (m, 1, CHN), 4.59 (t, J=4.9 Hz, 2OH), 3.34, 2.76 (each s, each 3, 2Me), 2.00 (m, 1, CH), 1.24, 1.22 (each d, J=6.5, 6.4 Hz, 2Me).

Anal. Calcd for $C_{20}H_{28}N_4O_3Cl_2·0.40 H_2O$: C, 53.31; H, 6.44; N, 12.43; Cl, 15.74. Found: C, 53.27; H, 6.42; N, 12.42; Cl, 15.89.

EXAMPLE 22

(1α, 2α, 4β)-[4-(4-Carboxy-5,6-dichloro-2-(isopropylamino)-1H-b enzimidazol-1-yl)-1,2-cyclopentylene]dimethanol By the method of Example 15, part c, (6a'-', 8a'-α, 7'-α)-5,6-dichloro-1-[hexahydrospiro(cyclohexene-1,3'-1H-cyclopenta[e][1,3]dioxepin)-7'-yl]-2-(isopropylamino)-1H-benzimidazole (1.0 g, 2.21 mmol) was lithiated at −78_C., stirred 0.5 h, then carbon dioxide (sublimation of dry ice through calcium chloride drying tube) was bubbled into the reaction at −78° C. for 2 h. The resulting slurry was carefully (CO$_2$ evolution) adjusted to pH 1 (iced N HCl), extracted with methylene chloride, and concentrated to dryness. Deprotection of the crude carboxylic acid as described in Example 19, concentration, and purification on LiChroprep RP-18 reverse phase silica gel (40–63 um, 50 g), eluting with 10% methanol-water to give the title compound (0.50 g, 50%) as a brittle solid, m.p. >250° C. (decomposition); $^1$H-NMR (DMSO-d$_6$) δ: 7.00 (s, 1, aromatic CH), 6.35 (d, J=7 Hz, 1, NH), 4.95 (m, 1, CHN), 4.65 (bs, 2OH), 4.05 (m, 1, CHN), 3.60–3.00 (m, 4, 2CH$_2$OH), 2.10–1.80 (m, 6, CH), 1.20 (d, J=6.5 Hz, 6, 2Me).

Anal. Calcd for $C_{18}H_{22}N_3O_4Cl_2Na·1.10 H_2O$: C, 47.19; H, 5.32; N, 9.17; Cl, 15.48; Found: C, 47.46; H, 5.25; N, 9.13; Cl, 15.12.

EXAMPLE 23

(1α, 2α, 4β)-[4-(4-Fluoro-5,6-dichloro-2-(isopropylamino)-1H-benzimidazol-1-yl)-1,2cyclopentylene]dimethanol By the method of Example 15, part c, (6a'-α, 8a'-α, 7'-α)-5,6-dichloro-1-[hexahydrospiro(cyclohexene-1,3'-1H-cyclopenta[e][1,3]dioxepin)-7'-yl]-2-(isopropylamino)1H-benzimidazole (1.0 g, 2.21 mmol) was lithiated then treated with N-fluorobenzenesulfonimide (0.70 g, 2.21 mmol, Allied Signal Corp.) and stirred 1 h. The reaction mixture was neutralized to pH 7 (1 N HCl), concentrated to dryness, then purified by chromatography on silica gel. Elution with methylene chloride afforded 0.70 g of a 2:1 mixture of (6a'-α, 8a'-α, 7'-α)-4-fluoro-5,6-dichloro-1-[hexahydrospiro (cyclohexene-1,3'-1H-cyclopenta[e][1,3]dioxepin)-7'-yl]-2-(isopropylamino)-1H-benzimidazole and starting material. This mixture was deprotected as described in Example 20, then acetylated using acetic anhydride (1.5 mL) and pyridine (20 mL) with stirring overnight. Workup as described Example 1, part e and chromatography using 20% ethyl acetate-hexanes allowed removal of lower Rf 4-H-benzimidazole. Deactylation was carried out-as described in Example 1, part f. Chromatography of the crude product using 10% methanol-chloroform and crystallization from ethanol-water provided the title compound as a white crystalline solid (0.140 g, 15% overall), m.p. 209–211° C.; $^1$H-NMR (DMSO-d$_6$) δ: 7.18 (s, 1, aromatic CH), 6.81 (bd, J=7.4 Hz, 1, NH), 4.98 (m, 1, NCH), 4.58 (t, J=5 Hz, 2, 2OH), 4.07 (m, 1, NCl-i-Pr), 3.58–3.32 (m, 4, 2 CH$_2$OH), 2.02 (m, 6, CH), 1.25 (d, J=6.4 Hz, 6, 2Me).

Anal. Calcd for $C_{17}H_{22}N_3O_2Cl_2F$: C, 52.32 H, 5.68; N, 10.77; Cl, 18.17, Found: C, 52.38; H, 5.72; N, 10.68; Cl, 18.09.

EXAMPLE 24

(1α, 2α, 4β)-[4(2-Methyl-1-propenyl)-5,6-dichloro-2-(isopropylamino)-1H-benzimidazol-1-yl)-1,2-cyclopentylene]dimethanol a) (6a'-α, 8a'-α, 7'-α)-[4-(2-Methyl-1-propenyl)-5,6-dichloro-1-[hexahydrospiro(cyclohexene-1,3'-1H-cyclopenta[e][1,3]dioxepin)-7'-yl]-2-(isopropylamino)]-1H-benzimidazole By the method of Example 15, part c, (6a'-α, 8a'-α, 7'-α)-5,6-dichloro-1-[hexahydrospiro(cyclohexene-1,3'-1H- cyclopenta[e][1,3]dioxepin)-7'-yl]-2-(isopropylamino)1H-benzimidazole (0.50 g, 1.05 mmol) was lithiated in tetrahydrofuran (7 mL) then treated with copper (1) bromide (0.100 g, 0.11 mmol). The dark reaction mixture was treated with isoprenyl bromide (0.60 mL, 5.55 mmol) and stirred 5 h at −78° C. at which point tlc (silica gel developed with 50% ethyl acetate-hexanes) indicated the presence of ca. 10% starting material. The reaction mixture was neutralized to pH 7, extracted with ethyl acetate, dried over sodium sulfate, and concentrated to dryness. Chromatography on silica gel, eluting with 20% ethyl acetate-hexanes afforded (6a'-α, 8a'-α, 7'-α)-[4-(2-methyl-1-propenyl)-5,6-dichloro-1-[hexahydro-spiro(cyclohexene-1,3'-1H-cyclopenta[e][1,3]dioxepin)-7-yl]-2-(isopropyl-amino)]-1H-benzimidazole as a white solid (0.40 g, 74%), m.p. 141–143° C.

Anal. Calcd for $C_{27}H_{37}N_3O_2Cl_2$: C, 64.02; H, 7.36; N, 8.30; Cl, 14.00. Found: C, 64.12; H, 7.43; N, 8.25; Cl, 13.92.

b) (1α, 2α, 4β)-[4-(2-Methyl-1-propenyl)-5,6-dichloro-2-(isopropylamino)-1H-benzimidazol-1-yl)-1,2-cyclopentylene]dimethanol (6a'-α, 8a'-α, 7'-α)-[4-(2-Methyl-1-propenyl)-5,6-dichloro-1-[hexahydrospiro (cyclohexene)-1,3'-1H-cyclopenta[e][1,3]dioxepiny-7'-yl]-2-(isopropylamino)]-1H-benzimidazole (0.300 g, Example 27, part a) was deprotected as described in Example 20. Chromatography on silica gel eluting with 10% methanol-chloroform afforded the title compound as a white solid (0.140 g, 65%), m.p. 90–92° C.; $^1$H-NMR (DMSO-$d_6$) δ: 7.20 (s, 1, aryl-H), 6.56 (d, J=7.3 Hz, 1, NH), 4.97 (m, 1, CHN), 4.72,4.50 (each bs, each 1, =CH$_2$), 4.58 (t, J=5.10 Hz, 2OH), 4.04 (m, 1, CHN), 3.68–3.42 (m, 4, 2CH$_2$OH), 3.68 (bs, 2, CH$_2$), 2.03 (m, 6, CH), 1.74 (s, 3, CHMe), 1.25 (d, J=6.4 Hz, 6, 2Me).

Anal. Calcd for $C_{21}H_{29}N_3O_2Cl_2$·0.30 $H_2O$: C, 58.41; H, 6.91; N, 9.73; Cl, 16.42. Found: C, 58.41; H, 6.88; N, 9.77; Cl, 16.48.

EXAMPLE 25

(1α, 2α, 4β)-[4-(2-Methyl-1-propyl)-5,6-dichloro-2-(isopropylamino)-1H-benzimidazol-1yl)-1,2-cyclopentylene]dimethanol (6a'-α, 8a'-α, 7'-α)-[4-(2-methyl-1-propenyl)-5,6-dichloro-1-[hexahydrospiro (cyclohexene-1,3'-1H-cyclopenta[e][1,3]dioxepin)-7'-yl]-2-(isopropylamino)]-1H-benzimidazole (0.40 g, prepared by the method of example 28, part a) was dissolved in ethanol (25 mL), treated with 10% palladium on carbon (60 mg) then hydrogenated in a Parr shaker at 40 psi for 12 hours. The catalyst was removed by filtration through Celite under reduced pressure. The colorless solution was concentrated to dryness and deblocked as described in example 20. Chromatography on silica gel, eluting with 10% methanol-chloroform and recrystallization from ethanol-water gave the title compound as a white solid (0.160 g, 51%), m.p. 100–102° C.; $^1$H-NMR (DMSO-$d_6$) δ: 7.16 (s, 1, aryl-H), 6.51 (d, J=7.3 Hz, 1, NH), 4.96 (m, 1, CHN), 4.58 (t, J=5.0 Hz, 2OH), 4.58 (m, 1, CHN), 3.68–3.42 (m, 4, 2CH$_2$OH), 2.87 (d, J=7 Hz, 2, CH$_2$CHMe$_2$), 2.18–1.95 (m, 7, CH), 1.25 (d, J=6.7 Hz, 6, 2Me), 0.89 (d, J=6.6 Hz, 6, 2Me).

Anal. Calcd for $C_{21}H_{31}N_3O_2Cl_2$·1.0 $H_2O$: C, 56.50 H; 7.45; N, 9.41; Cl, 15.88. Found: C, 56.48; H, 7.44; N, 9.26; Cl, 15.76.

EXAMPLE 26

Tablet Formulation

The following formulations A, B and C are prepared by wet granulation of the ingredients with a solution of povidone, followed by addition of magnesium stearate and compression.

Formulation A

|  | mg/tablet |
|---|---|
| Active Ingredient | 250 |
| Lactose B.P. | 210 |
| Povidone B.P. | 15 |
| Sodium Starch Glycollate | 20 |
| Magnesium Stearate | 5 |
|  | 500 |

Formulation B

|  | mg/tablet |
|---|---|
| Active Ingredient | 250 |
| Lactose B.P. | 150 |
| Avicel PH 101 | 60 |
| Povidone B.P. | 15 |
| Sodium Starch Glycollate | 20 |
| Magnesium Stearate | 5 |
|  | 500 |

Formulation C

|  | mg/tablet |
|---|---|
| Active Ingredient | 100 |
| Lactose B.P. | 200 |
| Starch | 50 |
| Povidone | 5 |
| Magnesium Stearate | 4 |
|  | 359 |

The following formulations, D and E, are prepared by direct compression of the admixed ingredients. The lactose in formulation E is of the direct compression type (Dairy Crest—"Zeparox").

Formulation D

|  | mg/tablet |
|---|---|
| Active Ingredient | 250 |
| Pregelatinized Starch NF15 | 150 |
|  | 400 |

Formulation E

|  | mg/tablet |
|---|---|
| Active Ingredient | 250 |
| Lactose B.P. | 150 |
| Avicel | 100 |
|  | 500 |

Formulation F (Controlled Release Formulation)

The formulation is prepared by wet granulation of the ingredients with a solution of povidone followed by the addition of magnesium stearate and compression.

|  | mg/tablet |
| --- | --- |
| Active Ingredient | 500 |
| Hydroxypropylmethylcellulose (Methocel K4M Premium) | 112 |
| Lactose B.P. | 53 |
| Povidone B.P. | 28 |
| Magnesium Stearate | 7 |
|  | 700 |

Drug release takes place over a period of about 6–8 hours and is complete after 12 hours.

EXAMPLE 27

Capsule Formulations

Formulation A

A capsule formulation is prepared by admixing the ingredients of formulation D in Example 1 above and filling into a two-part hard gelatin capsule. Formulation B (infra) is prepared in a similar manner.

Formulation B

|  | mg/capsule |
| --- | --- |
| Active Ingredient | 250 |
| Lactose B.P. | 143 |
| Sodium Starch Glycollate | 25 |
| Magnesium Stearate | 2 |
|  | 420 |

Formulation C

|  | mg/capsule |
| --- | --- |
| Active Ingredient | 250 |
| Macrogel 4000 B.P. | 350 |
|  | 600 |

Capsules of formulation C are prepared by melting the Macrogel 4000 B.P., dispersing the active ingredient in the melt and filling the melt into a two-part hard gelatin capsule.

Formulation D

|  | mg/capsule |
| --- | --- |
| Active Ingredient | 250 |
| Lecithin | 100 |
| Arachis Oil | 100 |
|  | 450 |

Capsules of formulation D are prepared by dispersing the active ingredient in the lecithin and arachis oil and filling the dispersion into soft, elastic gelatin capsules.

Formulation E (Controlled Release Capsule)

The following controlled release capsule formulation is prepared by extruding ingredients a, b, and c using an extruder, followed by spheronization of the extrudate and drying. The dried pellets are then coated with release-controlling membrane (d) and filled into a two-piece, hard gelatin capsule.

|  |  | mg/capsule |
| --- | --- | --- |
| (a) | Active Ingredient | 250 |
| (b) | Microcrystalline Cellulose | 125 |
| (c) | Lactose B.P. | 125 |
| (d) | Ethyl Cellulose | 13 |
|  |  | 513 |

EXAMPLE 28

Injectable Formulation

Formulation A

|  | mg |
| --- | --- |
| Active Ingredient | 200 |
| Hydrochloric Acid Solution 0.1 M or Sodium Hydroxide Solution 0.1 M q.s. to pH | 4.0 to 7.0 |
| Sterile water q.s. to | 10 ml |

The active ingredient is dissolved in most of the water (35–40° C.) and the pH adjusted to between 4.0 and 7.0 with the hydrochloric acid or the sodium hydroxide as appropriate. The batch is then made up to volume with the water and filtered through a sterile micropore filter into a sterile 10 ml amber glass vial (type 1) and sealed with sterile closures and overseals.

Formulation B

| Active Ingredient | 125 mg |
| --- | --- |
| Sterile, Pyrogen-free, pH 7 Phosphate Buffer, q. s. to | 25 ml |

EXAMPLE 29

Intramuscular injection

| Active Ingredient | 200 mg |
| --- | --- |
| Benzyl Alcohol | 0.10 g |
| Glycofurol 75 | 1.45 g |
| Water for injection q.s. to | 3.00 ml |

The active ingredient is dissolved in the glycofurot. The benzyl alcohol is then added and dissolved, and water added to 3 ml. The mixture is then filtered through a sterile micropore filter and sealed in sterile 3 ml amber glass vials (type 1).

EXAMPLE 30

Syrup

| Active Ingredient | 250 mg |
| --- | --- |
| Sorbitol Solution | 1.50 g |
| Glycerol | 2.00 g |
| Sodium Benzoate | 0.005 g |
| Flavor, Peach 17.42.3169 | 0.0125 ml |
| Purified Water q.s. to | 5.00 ml |

The active ingredient is dissolved in a mixture of the glycerol and most of the purified water. An aqueous solution

EXAMPLE 31

Suppository

|  | mg/capsule suppository |
|---|---|
| Active Ingredient | 250 |
| Hard Fat, B.P. (Witepsol H15 - Dynamit Nobel) | 1770 |
|  | 2020 |

One-fifth of the Witepsol H15 is melted in a steam-jacketed pan at 45° C. maximum. The active ingredient is sifted through a 200 μM sieve and added to the molten base with mixing, using a Silverson fitted with a cutting head, until a smooth dispersion is achieved. Maintaining the mixture at 45° C., the remaining Witepsol H15 is added to the suspension and stirred to ensure a homogenous mix. The entire suspension is passed through a 250 μm stainless steel screen and, with continuous stirring, is allowed to cool to 40° C. At a temperature of 38° C. to 40° C., 2.02 g of the mixture is filled into suitable, 2 ml plastic molds. The suppositories are allowed to cool to room temperature.

EXAMPLE 32

Pessaries

|  | mg/pessary |
|---|---|
| Active Ingredient | 250 |
| Anhydrate Dextrose | 380 |
| Potato Starch | 363 |
| Magnesium Stearate | 7 |
|  | 1000 |

The above ingredients are mixed directly and pessaries prepared by direct compression of the resulting mixture.

EXAMPLE 33

Antiviral Activity (a) CMV Assay

Human cytomegalovirus (HCMV) was assayed in monolayers of MRC5 cells (human embryonic lung) in multiwell trays. The standard CMV strain AD 169 was used. Activity of compounds is determined in the plaque reduction assay, in which a cell monolayer is infected with a suspension of HCMV, and then overlaid with nutrient carboxymethyl cellulose in the form of a gel to ensure that there is no spread of virus throughout the culture. A range of concentrations of compound of known molarity was incorporated in the nutrient overlay. Plaque numbers at each concentration of drug are expressed as percentage of the control and a dose-response curve is drawn.

(b) Cell Toxicity

Cell toxicity is assessed in cell growth inhibition assay. Subconfluent cultures of Vero cells grown on 96-well microtiter dishes are exposed to different dilutions of drug, and cell viability determined daily on replicate cultures using uptake of a tetrazolium day (MTT). The concentration required for 50% inhibition of cell viability at 96 hours is termed $CCID_{50}$.

We claim:

1. A compound of formula (I).

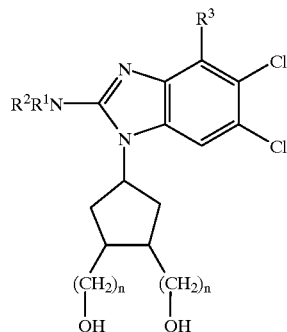

wherein:

$R^1$ represents;

H, $C_{1-4}$ alkyl, $C_{3-5}$ cycloalkyl;

$R^2$ represents;

H, $C_{1-4}$ alkyl; or $R^1$ and $R^2$ together form with the nitrogen a 4 or 5 membered heterocyclic ring;

$R^3$ represents $BR^4$ or $R^4$ wherein B represents a bridging group —C(O)NH—, —C(O)N$C_{1-4}$alkyl-, or —C(O)O— and $R^4$ represents H, $C_{1-4}$alkyl, $C_{2-6}$alkenyl or halo; and each n is an integer independently selected from 0, 1, or 2; and geometric isomers or mixtures thereof; and physiologically functional derivatives thereof.

2. A compound of formula (I) according to claim 1 wherein $R^1$ is cyclopropyl and $R^2$ is H.

3. A compound of formula (I) according to claim 1 wherein either $R^1$ or $R^2$ is H and the other $R^1$ and $R^2$ group represents isopropyl.

4. A compound of formula (I) according to claim 1 wherein either $R^1$ or $R^2$ is H and the other $R^1$ or $R^2$ group represents tert-butyl.

5. A compound of formula (I) according to claim 1, wherein $R^1$ and $R^2$ together with the nitrogen form an azetidenyl group.

6. A compound of formula (I) according to claim 1, wherein $R^3$ is F and n is 0 or 1.

7. A compound of formula (I) according to claim 1, wherein $R^3$ is $C_{1-4}$alkyl or $C_{2-6}$alkenyl and n is 0 or 1.

8. The compound according to claim 1, wherein each n is an integer independently selected from 0 or 1.

9. A compound of formula (I) according claim 1 in the 1α, 2α, 4β or 1β, 2β, 4α geometeric form.

10. A compound of formula (I) according to claim 1 selected from:

(1α, 2α, 4β)-4-[5,6-Dichloro-2-(cyclopropylamino)-1H-benzimidazol-1-yl]-1,2-cyclopentanediol;

(1 b, 2b, 4a)-4-[5,6-Dichloro-2-(isopropylamino)1H-benzimidazol-1-yl]-1,2-cyclopentanediol;

(1b, 2b, 4a)-4-[5,6-Dichloro-2-(azetidinyl)-1H-benzimidazol-1-yl]-1,2-cyclopentanediol; and (1b, 2b, 4a)-4-[5,6-Dichloro-2-(tert-butylamino)-1H-benzimidazol-1-yl]-1,2-cyclopentanediol.

(1α, 2α, 4β)-[4-(5, 6-Dichloro-2-(cyclopropylamino)-1H-benzimidazol-1-yl)-1,2-cyclopentylene] dimethanol;

(1α, 2α, 4β)-[4-5,6-Dichloro-2-(isopropylamino)-1H-benzimidazol-1-yl)-1,2-cyclopentylene]dimethanol;

(1α, 2α, 4β)-[4(4-Fluoro-5,6dichloro-2-(isopropylamino-1H-benzimidazol-1-yl)-1,2-cyclopentylene]dimethanol.

11. A pharmaceutical formulation comprising a compound of formula (I) according to claim 1 and a pharmaceutically acceptable carrier thereof.

12. A process for producing a compound of formula (I) as defined in claim 1 or a physiologically functional derivative thereof, said process comprising:

reacting a compound of formula (II)

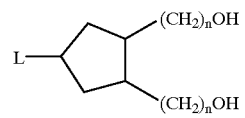
(II)

wherein $R^1$ is selected from the group consisting of H, $C_{1-4}$alkyl, and $C_{3-5}$ cycloalkyl;

$R^2$ is H or $C_{1-4}$alkyl; or $R^1$ and $R^2$ together with the nitrogen form a 4 or 5 membered heterocyclic ring; and $R^3$ is $BR^4$ or $R^4$ wherein B is a bridging group selected from —C(O)NH—, 'C(O)N$C_{1-4}$ alkyl-, and —C(O)O— and $R^4$ is selected from the group consisting of H, $C_{1-4}$alkyl, $C_{2-6}$ alkenyl and halo;

with a compound of formula (III) or a protected form thereof

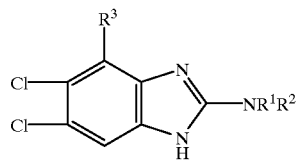
(III)

wherein L is a leaving group and n is an integer selected from 0, 1, and 2.

13. A compound of formula (V)

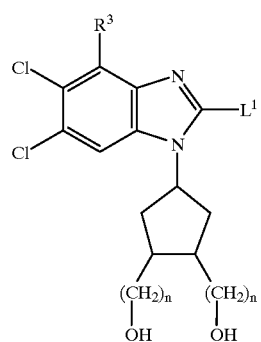
(V)

wherein $L^1$ represents a halo group; $R^3$ represents I, Cl, Br, F, $CH_3$ or H and n is an integer 0, 1 or 2.

* * * * *